US010342800B2

(12) United States Patent
Wilhelm-Ogunbiyi et al.

(10) Patent No.: US 10,342,800 B2
(45) Date of Patent: *Jul. 9, 2019

(54) DOSING REGIMEN FOR SEDATION WITH CNS 7056 (REMIMAZOLAM)

(71) Applicant: PAION UK Limited, Histon Cambridge (GB)

(72) Inventors: Karin Wilhelm-Ogunbiyi, Simmermath (DE); Keith Borkett, Houghton Camps (GB); Gary Stuart Tilbrook, Huntingdon (GB); Hugh Wiltshire, Digswell (GB)

(73) Assignee: PAION UK LTD., Histon, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/213,879

(22) Filed: Dec. 7, 2018

(65) Prior Publication Data

US 2019/0111062 A1 Apr. 18, 2019

Related U.S. Application Data

(63) Continuation of application No. 16/039,198, filed on Jul. 18, 2018, now Pat. No. 10,195,210, which is a continuation of application No. 15/792,636, filed on Oct. 24, 2017, now Pat. No. 10,052,334, which is a continuation of application No. 15/647,143, filed on Jul. 11, 2017, now Pat. No. 9,827,251, which is a continuation of application No. 15/400,117, filed on Jan. 6, 2017, now Pat. No. 9,737,547, which is a continuation of application No. 13/883,935, filed as application No. PCT/EP2011/005581 on Nov. 7, 2011, now Pat. No. 9,561,236.

(30) Foreign Application Priority Data

| Nov. 8, 2010 | (EP) | 10014366 |
| Nov. 19, 2010 | (EP) | 10014784 |
| Nov. 22, 2010 | (EP) | 10014819 |
| Nov. 25, 2010 | (EP) | 10014972 |

(51) Int. Cl.
| *A61K 31/5517* | (2006.01) |
| *A61K 31/4468* | (2006.01) |
| *A61K 45/06* | (2006.01) |
| *A61K 9/00* | (2006.01) |

(52) U.S. Cl.
CPC ........ *A61K 31/5517* (2013.01); *A61K 9/0019* (2013.01); *A61K 31/4468* (2013.01); *A61K 45/06* (2013.01)

(58) Field of Classification Search
CPC .................................................. A61K 31/5517
See application file for complete search history.

(56) References Cited

U.S. PATENT DOCUMENTS

| 3,520,877 A | 7/1970 | Fryer |
| 3,795,673 A | 3/1974 | Meguro et al. |
| 3,933,794 A | 1/1976 | Hester, Jr. et al. |
| 4,133,809 A | 1/1979 | Vogt |
| 4,427,590 A | 1/1984 | Allgeier et al. |
| 4,487,771 A | 12/1984 | Baglioni |
| 4,489,003 A | 12/1984 | Hunkeler et al. |
| 4,621,083 A | 11/1986 | Casals-Stenzel et al. |
| 4,724,237 A | 2/1988 | Bock et al. |
| 4,755,508 A | 7/1988 | Bock et al. |
| 4,820,834 A | 4/1989 | Evans et al. |
| 5,019,583 A | 5/1991 | Feldman et al. |
| 5,185,331 A | 2/1993 | Freidinger et al. |
| 5,220,017 A | 6/1993 | Bock et al. |
| 5,324,726 A | 6/1994 | Bock et al. |
| 5,550,126 A | 8/1996 | Horwell et al. |
| 5,665,718 A | 9/1997 | Godel et al. |
| 5,698,691 A | 12/1997 | Yukimasa et al. |
| 5,753,649 A | 5/1998 | Tahara et al. |
| 5,834,464 A | 11/1998 | Bock et al. |
| 6,222,032 B1 | 4/2001 | Bertrand et al. |
| 6,544,983 B2 | 4/2003 | Doherty |
| 6,916,923 B2 | 7/2005 | Ding et al. |
| 7,160,880 B1 | 1/2007 | Feldman et al. |
| 7,435,730 B2 | 10/2008 | Feldman et al. |
| 7,473,689 B2 | 1/2009 | Feldman et al. |
| 7,485,635 B2 | 2/2009 | Feldman et al. |

(Continued)

FOREIGN PATENT DOCUMENTS

| CH | 608234 A5 | 12/1978 |
| CN | 101501019 A | 8/2009 |

(Continued)

OTHER PUBLICATIONS

"9-Fluorenylmethyl Carbamate, t-Butyl Carbamate" in: Greene, T.W.; Wuts, P.G.M.: "Protective Groups in Organic Synthesis" 1999, John Wiley & Sons Inc., New York, Chichester, Weinheim, Brisbane, Toronto, Singapore, XP002563125, ISBN: 0471160199, 8 pages.
"Dose-Finding Safety Study Evaluating CNS 7056 in Patients Undergoing Diagnostic Upper GI Endoscopy", ClinicalTrials.gov, Anonymous, Sep. 8, 2010, 1-4.
Antonik, L. J. et al., "A Placebo- and Midazolam-Controlled Phase I Single Ascending-Dose Study Evaluating the Safety, Pharmacokinetics, and Pharmacodynamics of Remimazolam (CNS 7056): Part I. Safety, Efficacy, and Basic Pharmacokinetics," Anesthesia & Analgesia, (2012), 115(2):274-283.
Avdagic, Amir et al., "Lipase-catalyzed acetylation of 3-substituted 2,3-dihydro-1H-1,4-bezodiazepin-2-ones. Effect of temperature and conformation on enantioselectivity and configuration", Helv. Chim. Acta, vol. 81, No. 8, pp. 1567-1582, (1998).

(Continued)

*Primary Examiner* — Svetlana M Ivanova
(74) *Attorney, Agent, or Firm* — Mintz Levin Cohn Ferris Glovsky and Popeo PC

(57) ABSTRACT

The invention relates to a dosing regimen for sedation with the fast-acting benzodiazepine CNS 7056 in combination with an opioid, in particular fentanyl, whereas CNS 7056 is given in a dose of 2 to 20 mg, preferably between 4 and 9 mg and most preferably between 5 and 8 mg.

28 Claims, 7 Drawing Sheets

(56) References Cited

U.S. PATENT DOCUMENTS

Figure 2:
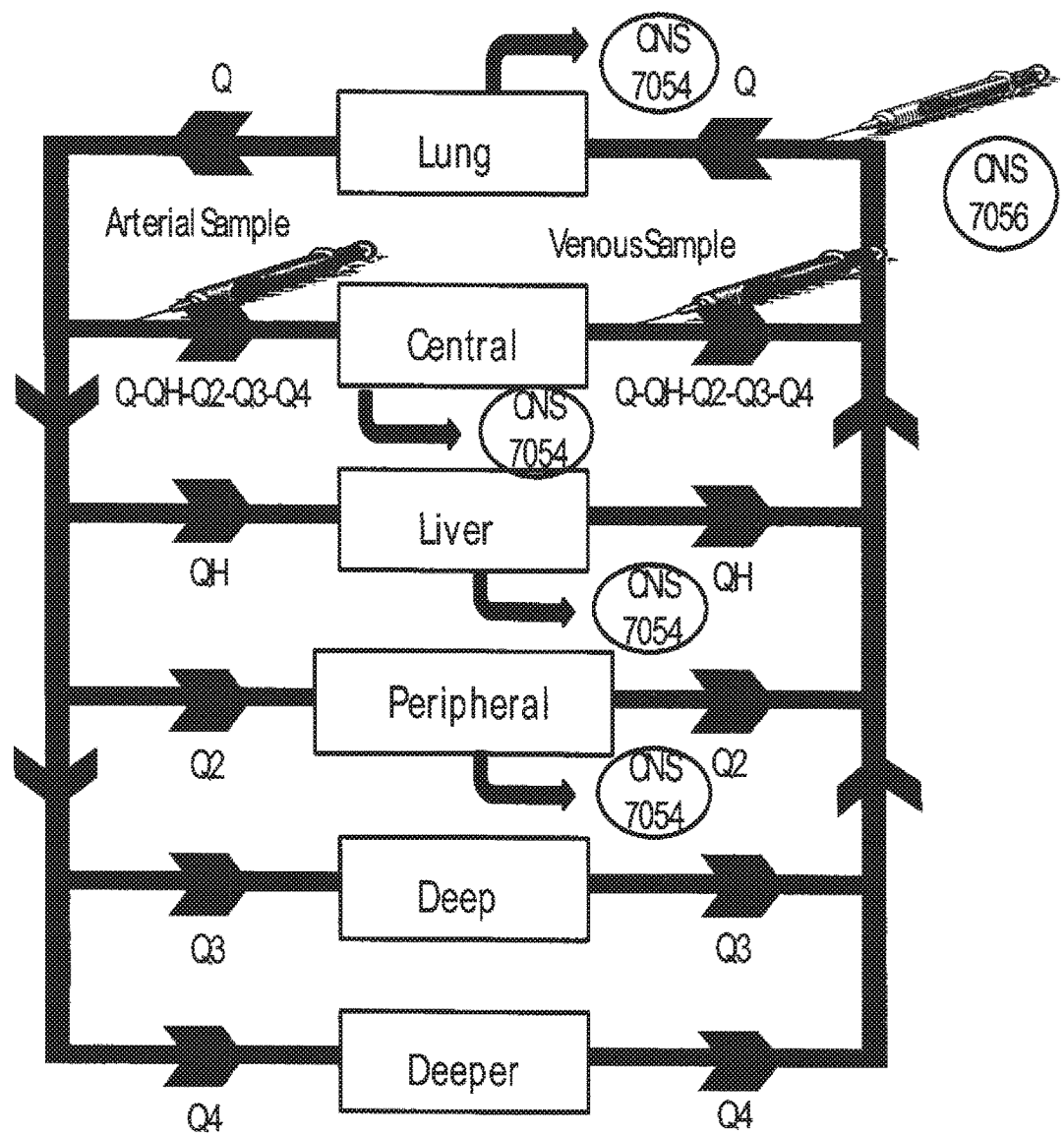

| | | | |
|---|---|---|---|
| 7,528,127 | B2 | 5/2009 | Feldman et al. |
| 7,625,948 | B2 | 12/2009 | Hagiwara et al. |
| 7,951,798 | B2 | 5/2011 | Petho et al. |
| 8,039,460 | B2 | 10/2011 | Burgey et al. |
| 8,642,588 | B2 | 2/2014 | Tilbrook et al. |
| 9,050,622 | B2 | 6/2015 | Aitken et al. |
| 9,156,842 | B2 | 10/2015 | Tilbrook et al. |
| 9,193,730 | B2 | 11/2015 | Tilbrook et al. |
| 9,440,025 | B2 | 9/2016 | Kanderian, Jr. et al. |
| 9,512,078 | B2 | 12/2016 | Tilbrook et al. |
| 9,561,236 | B2 * | 2/2017 | Wilhelm-Ogunbiyi .................. A61K 31/4468 |
| 9,737,547 | B2 * | 8/2017 | Wilhelm-Ogunbiyi .................. A61K 31/4468 |
| 9,777,007 | B2 | 10/2017 | Tilbrook et al. |
| 9,827,251 | B1 * | 11/2017 | Wilhelm-Ogunbiyi .................. A61K 31/4468 |
| 9,838,177 | B2 | 12/2017 | Sun et al. |
| 9,914,738 | B2 | 3/2018 | Tilbrook et al. |
| 10,052,334 | B2 * | 8/2018 | Wilhelm-Ogunbiyi .................. A61K 31/4468 |
| 10,195,210 | B2 * | 2/2019 | Wilhelm-Ogunbiyi .................. A61K 31/4468 |
| 2002/0055500 | A1 | 5/2002 | Wu et al. |
| 2006/0094652 | A1 | 5/2006 | Levy et al. |
| 2006/0198896 | A1 | 9/2006 | Liversidge et al. |
| 2007/0093475 | A1 | 4/2007 | Feldman et al. |
| 2010/0075955 | A1 | 3/2010 | Tilbrook et al. |
| 2010/0081647 | A1 | 4/2010 | Tilbrook et al. |
| 2011/0294843 | A1 | 12/2011 | Sohngen et al. |
| 2012/0330007 | A1 | 12/2012 | Tilbrook et al. |
| 2014/0080815 | A1 | 3/2014 | Wilhelm-Ogunbiyi et al. |
| 2015/0006104 | A1 | 1/2015 | Okada et al. |
| 2015/0148338 | A1 | 5/2015 | Graham et al. |
| 2015/0224114 | A1 | 8/2015 | Kondo et al. |
| 2015/0368199 | A1 | 12/2015 | Tilbrook et al. |
| 2016/0009680 | A1 | 1/2016 | Kawakami et al. |
| 2016/0176881 | A1 | 6/2016 | Tilbrook et al. |
| 2017/0044135 | A1 | 2/2017 | Tilbrook et al. |
| 2018/0042939 | A1 | 2/2018 | Wilhelm-Ogunbiyi et al. |

FOREIGN PATENT DOCUMENTS

| | | |
|---|---|---|
| EP | 167919 A2 | 1/1986 |
| EP | 0264797 A2 | 4/1988 |
| EP | 434360 A1 | 6/1991 |
| EP | 434364 A2 | 6/1991 |
| EP | 523845 A2 | 1/1993 |
| FR | 2034577 A1 | 12/1970 |
| FR | 2183716 A1 | 12/1973 |
| FR | 2414043 A1 | 8/1979 |
| GB | 2259013 A | 3/1993 |
| JP | 2011153104 A | 8/2011 |
| WO | WO-8910127 A1 | 11/1989 |
| WO | WO-9105549 A1 | 5/1991 |
| WO | WO-9620941 A1 | 7/1996 |
| WO | WO-9623790 A1 | 8/1996 |
| WO | WO-9741896 A2 | 11/1997 |
| WO | WO-9800405 A1 | 1/1998 |
| WO | WO-0069836 A1 | 11/2000 |
| WO | WO-05077072 A2 | 8/2005 |
| WO | WO-2006010620 A2 | 2/2006 |
| WO | WO-2006044504 A1 | 4/2006 |
| WO | WO-2006078554 A2 | 7/2006 |
| WO | WO-2008007071 A1 | 1/2008 |
| WO | WO-2008007081 A1 | 1/2008 |
| WO | WO-2008147815 A1 | 12/2008 |
| WO | WO-2009145323 A1 | 12/2009 |
| WO | WO-2010116794 A1 | 10/2010 |
| WO | WO-2011032692 A1 | 3/2011 |
| WO | WO-2011054845 A1 | 5/2011 |
| WO | WO-2012062439 A1 | 5/2012 |
| WO | WO-2013029431 A1 | 3/2013 |
| WO | WO-2013174883 A1 | 11/2013 |

OTHER PUBLICATIONS

Baheti, A. et al., "Excipients used in lyophilization of small molecules," Journal of Excipients and Food Chem., 2010, vol. 1, 41-54.
Bard, James W., "The BIS monitor: a review and technology assessment." AANA journal 69.6 (2001): 477-484.
Bauer, T.M., et al. "Prolonged Sedation Due to Accumulation of Conjugated Metabolites of Midazolam." Lancet 1995, 346, pp. 145-147.
Bock, Mark G. et al., "Curtius rearrangement in the 5-phenyl-1,4-benzodiazepine series. Unprecedented participation by an image nitrogen", Journal Heterocycl. Chem., vol. 27, No. 3, (1990), pp. 631-636.
Bodor, N. et al., "Retrometabolic drug design: Principles and recent developments," Pure Appl. Chem., (2008), 80(8):1669-1682.
Bodor, N. et al., "Soft Drug Design: General Principles and Recent Applications," Medicinal Research Reviews, (2000), 20(1):58-101.
Chambon et al., "Ethyl Loflazepate: A Prodrug from the Benzodiazepine Series Designed to Dissociate Anxiolytic and Sedative Activities," Drug Res, 35 (II) Nr. 10, 1985, 1572-1577.
Corbella, Attilio et al., "Stereochemistry of the enzymic 3-hydroxylation of 1,3-dihydro-22H-1,4-benzodiazepin-2-ones", J. Chem. Soc., Chem. Commun., No. 19, (1973), pp. 721-722.
Crowley, et al., "Effects of excipients on the stability of medicinal products," Chemistry Today, 2010, vol. 28, VII-XIII.
Crowley, P., "Excipients as Stabilizers," Pharmaceutical Science and Technology Today, 1999, vol. 2, 237-243.
Dingemanse, J. et al. "Pharmacokinetic-Pharmacodynamic Modelling of the EEF Effects of RO 48-6791, a New Short-Acting Benzodiazepine, in Young and Elderly Subjects." Br. J. Anaesth. 1997, 79, pp. 567-574.
Dorwald, F. Zaragoza, "Side Reactions in Organic Synthesis: A Guide to Successful Synthesis Design," Weinheim: Wiley-VCH Verlag GmbH & Co. KGaA, (ISBN:3-527-31021-5) Preface, 6 pages (2005).
Dr H: "Relative Strengths of the Opioids", Heroin Helper, Jan. 8, 2004, www.heroinhelper.com/curious/pharmacology.
Feldman et al., "Design, Synthesis, and Pharmacological Evaluation of Ultrashort-to Long-Acting Opioid Analgetics,", J.Med.Chem., 1991,34, 2202-2208.
Fryer, et al., "Conformational Shifts at the Benzodiazepine Receptor Related to the Binding of Agonists antagonists and Inverse Agonists," Life Science, vol. 39, Pergamon Journals Ltd., 1986, 1947-1957.
Goodman et al., "The Pharmacological Basis of Therapeutics" Eighth Edition, 1990, 303-305, 346-358.
Goumri-Magnet S. Et al., "Free and Supported Phosphorus Ylides as Strong Neutral Bronsted Bases", Journal of Organic Chemistry, vol. 64, No. 10, (1999), pp. 3741-3744.
Greenblatt, D. et al., "Effect of Age, Gender, and Obesity in Midazolam Kinetics," Anesthesiology, (1984), 61:27-35.
Gutkin, Ellen, et al., "Pillcam ESO® is more accurate than clinical scoring systems in risk stratifying emergency room patients with acute upper gastrointestinal bleeding." *Therapeutic advances in gastroenterology* 6.3 (2013): 193-198.
Hayashi M., et al., "Oxidative Conversion of Silyl Enol Ethers to alpha- beta-Unsaturated Ketones Employing Oxoammonium Salts," Organic Letters, vol. 14(1), pp. 154-157 (2012).
Hayashi, M. et al., "9-Azanoradamantane N-Oxyl (Nor-AZADO): A Highly Active Organocatalyst for Alcohol Oxidation," Chem. Pharm. Bull., vol. 59(12), pp. 1570-1573 (2011).
Heaney Frances et al., "Steric control of reactivity: formation of oximes, benzodiazepinone N-oxides and isoxazoloquinolinones", Journal Chem. Soc., Perkin Trans. vol. 2, (3), (1998), pp. 547-559.
Hering W., et al. "CNS Effects of the New Benzodiazepines RO 48-6791 and RO 48-8684 Compared to Midazolam in Young and Elderly Volunteers." Anesthesiology 1996, 189,85 (Suppl.).
Hester, et al., "8-Chloro-1-methyl-6-phenyl-4H-s-triazolo [4,3-a][1,4] benzodiazepines with Subslituents at C4," J. Med Chem., 1980, 23, 643-647.
Huali, W. et al., "Advances in the study of the stability of lyophilized formulations," Chinese Journal of Pharmaceutical Sciences, vol. 36(7)(Section 2):436-438 (Jul. 31, 2001). with English Translation (16 pages).

(56) References Cited

OTHER PUBLICATIONS

Ichihara, Masato et al., "Preparation of diazepine derivatives as specific inhibitors of human renin", Database Chemabs Online, Chemical Abstracts Service,(1995) (4 Pages).
International Preliminary Report of PCT/EP2010/005668, dated Mar. 8, 2012 (24 Pages).
International Search Report, PCT/EP2010/005668, dated Dec. 3, 2010, 4 pages.
International Search Report, PCT/JP2014/055329, dated Apr. 8, 2014, pp. 5.
Johnson, Ken B. "New horizons in sedative hypnotic drug development: fast, clean, and soft." Anesthesia & Analgesia 115.2 (2012): 220-222.
Jordan, V. C., "Tamoxifen: A Most Unlikely Pioneering Medicine," Nature Reviews: Drug Discovery, vol. 2, pp. 205-213 (2003).
Kelly et al., Fentanyl midazolam combination for endoscopy sedation is safe and effective, Gastroenterology, vol. 114, Apr. 15, 1998, p. A22.
Khan et al., "Synthesis of 3-Substituted 1, 4-Benzodiazeptine-2-ones", Organic Preparations and Procedures Int. 10(3), 105-111, (1978).
Kharasch Evan D., "Opioid Half-Lives and Hemlines: The Long and Short of Fashion", Anesthesiology, May 2015, vol. 122, No. 5, pp. 969-970.
Kilpatrick, et al., "A Novel Ultra-Short-acting Benzodiazepine", Anesthesiology, 2007, vol. 107, 60-66.
Kilpatrick, G.J. et al., "Drug development in anaesthesia: industrial perspective," Curr. Opin. Anaesth., (2006), 19(4):385-389.
Krejcie, Tom C., and Michael J. Avram, "Recirculatory pharmacokinetic modeling: what goes around, comes around." Anesthesia & Analgesia 115.2 (2012): 223-226.
Lee, et al, "The Protective Effect of Lactose and Lyophilization of CNK-20402," AAPS Pharm Sci Tech., 2005, vol. 6. E42-E48.
Longcroft-Wheaton, et al., "S1421: The Safety and Efficacy of a Novel Sub-Mucosal Injection Solution: Results From a Large Prospective EMR Series." *Gastrointestinal Endoscopy* 71.5 (2010): AB157. (Abstract Only).
Manghisi, E. et al., Synthesis and central nervous effects of some 3-substituted 1,4-benzodiazepin-2-ones, Boll Chi. Farm., vol. 113, No. 12, (1974), pp. 642-644.
Nakajima, Hitoshi, et al., "S1418: Case Sensitive Confirmation of Colitis in Viral Gastroenteritis Suggests Clue to Clarify Acute Colitis." *Gastrointestinal Endoscopy* 71.5 (2010): AB156. (Abstract Only).
NCT00869440, Dose-Finding Safety Study Evaluating CNS 7056 in Patients Undergoing Diagnostic Upper GI Endoscopy, http://www.clinictrials.gov/ct2/show/NCT00869440?term=CNS 7056 &rank=2, update dated Sep. 8, 2010.
Ochs, et al., "Comparative Single-Dose Kinetics of Oxazolam, prazepam, and clorazepate: three precursors of desmethyldiazepam," J. Clin. Phannacol, 1984, vol. 24, 446-451.
Ono Pharmaceutical Co., Ltd., "Results of Phase II/III Study of ONO-2745/CNS7056, a Short-Acting General Anesthectic," Press Release of Ono Pharmaceutical Co., Ltd. issued Nov. 14, 2013, 2 pages.
P Wipf: "I. Basic Principles ID, Oxidation Reaction", Apr. 2, 2006, XP002563124; Retrieved from the Internet: URL: ccc.chem.pitt.edu/wipf/Courses/23206-file; 2.sup.nd Slide, p. 1, 5, 7.
Pace, V. et al., First General Route to Substituted a-Arylamino-a'-chloropropan-2-ones by Oxidation of N-Protected Aminohalohydrins: The Importance of Disrupting Hydrogen Bond Networks, Synthesis, vol. 20, pp. 3545-3555 (2010).
Pacofsky, G.J. et al., "Relating the structure, activity, and physical properties of ultrashort-acting benzodiazepine receptor agonists," Bioorg. Med. Chem. Lett., (2002), 12(21):3219-3222.
Paion's Phase IIb Study With Its Anaesthetic/Sedative Remimazolam (CNS 7056) Ahead of Schedule, Aug. 2, 2010, p. 1-2, htt12://www.paion.com/images/stories/investoren/finanznachrichten/2010/paionp100802en.pdf.

PCT International Search Report and Written Opinion dated Jan. 19, 2012 issued by the European Patent Office in International Application No. PCT/EP2011/005581 (4 Pages).
Riff, Dennis S., et al., "S1419: A Phase IIa, Randomized, Controlled, Double-Blind, Dose-Finding Study Evaluating the Safety and Pharmacodynamics of CNS 7056 in Patients Undergoing Diagnostic Upper Gi Endoscopy," Gastrointestinal Endoscopy, vol. 71, Issue 5, Apr. 2010. (Abstract Only).
Rigaux, Johanne, et al., "A novel system for the improvement of colonic cleansing during colonoscopy." *Endoscopy* 44.07 (2012): 703-706.
Sagara,G., "Results of Phase II Study of Ono-2745/CNS 7056, a short-acting General Anesthetic," Press Release of Ono Pharmaceutical Co., Ltd. issued May 14, 2012, 2 pages.
Shafer, A., et al. "Complications of Sedation with Midazolam in the Intensive Care Unit and a Comparison with Other Sedative Regimens." Crit. Care Med., 1998, 26, 947-956.
Shibuya M., et al., "Oxidation of nitroxyl radicals: electrochemical and computational studies," Tetrahedron Letters, vol. 53(16), pp. 2070-2073 (2012).
Shibuya, M. et al., "2-Azaadamantane N-Oxyl (AZADO): Highly efficient organocatalysts for oxidation of alcohols," Journal of the American Chemical Society, vol. 128, pp. 8412-8413 (2006).
Shibuya, M. et al., "Highly Efficient, Organocatalytic Aerobic Alcohol Oxidation," Journal of American Chemical Society, vol. 133, pp. 6497-6500 (2011).
Shimamoto, Kiro et al., "Pharmaceutical screening of new benzodiazepines in mice", Takeda Kenkyusho Ho, vol. 29, No. 1 (1970) pp. 134-144.
Sneyd, J. Robert, "Remimazolam: new beginnings or just a metoo?." Anesthesia & Analgesia 115.2 (2012): 217-219.
Sofuni, Atsushi, et al., "Effectiveness of Prophylaxis of Post-ERCP Pancreatitis for Risk Group by Endoscopic Pancreatic Spontaneous Dislodgement Stent-Randomized Controlled Multicenter Trial," Endoscopy, 41 (Suppl 1), 2009.
Stafford, J.A. et al. "Identification and structure-activity studies of novel ultrashort-acting benzodiazepine receptor agonists," Bioorg. Med. Chem. Lett.,(2002), 12(21):3215-3218.
Stahl, "Handbook of Pharmaceutical Salts," (2002), pp. 263-265, 272, 273, 280 and 281.
Stahl, et al., "Handbook of Pharmaceutical Salts: Properties, Selection, and Use," 2002, 164-167 and 272-273.
Thompson, Diane O., "Cyclodextrins-Enabling Excipients: Their Present and Future Use in Pharmaceuticals," Critical Reviews in Therapeutic Drug Carrier Systems, 1997, vol. 14(1), 1-108.
Tsiakitzis, et al., "Novel Compounds Designed as Antistress Agents," Journal of Medicinal Chemistry, vol. 52, 2009, 7315-7318.
U.S. Appl. No. 09/980,680, filed Oct. 31, 2001, Paul L Feldman (89 Pages).
U.S. Appl. No. 11/634,788, filed Dec. 5, 2006, Paul L. Feldman (90 Pages).
U.S. Appl. No. 11/650,635, filed Jan. 5, 2007, Paul L. Feldman (90 Pages).
U.S. Appl. No. 11/650,636, filed Jan. 5, 2007, Paul L. Feldman (94 Pages).
U.S. Appl. No. 11/650,637, filed Jan. 5, 2007, Paul L. Feldman (96 Pages).
U.S. Appl. No. 12/373,457, filed Nov. 13, 2009, Gary Stuart Tilbrook (28 Pages).
U.S. Appl. No. 12/373,472, filed Nov. 2, 2009, Gary Stuart Tilbrook (69 Pages).
U.S. Appl. No. 13/124,476, filed Aug. 15, 2011, Mariola Sohngen (41 Pages).
U.S. Appl. No. 13/496,742, filed Aug. 30, 2012, Gary Stuart Tilbrook (28 Pages).
U.S. Appl. No. 13/883,935, filed Sep. 10, 2013, Karin Wilhelm-Ogunbiyi (58 Pages).
U.S. Appl. No. 14/402,590, filed Nov. 20, 2014, John Aitken Graham (76 Pages).
U.S. Appl. No. 14/424,340, filed Feb. 26, 2015, Maki Kondo (85 Pages).
U.S. Appl. No. 14/746,026, filed Jun. 22, 2015, Gary Stuart Tilbrook (66 Pages).

(56) References Cited

OTHER PUBLICATIONS

U.S. Appl. No. 14/772,203, filed Sep. 2, 2015, Yuji Kawakami (49 Pages).
U.S. Appl. No. 14/841,899, filed Sep. 1, 2015, Gary Stuart Tilbrook (29 Pages).
U.S. Appl. No. 14/948,889, filed Nov. 23, 2015, Gary Stuart Tilbrook (67 Pages).
U.S. Appl. No. 15/336,143, filed Oct. 27, 2016, Gary Stuart Tilbrook (34 Pages).
U.S. Non-Final Office Action dated Mar. 23, 2017 in U.S. Appl. No. 14/948,889 (12 Pages).
U.S. Notice of Allowance on U.S. Appl. No. 14/948,889 dated Aug. 16, 2017 (5 Pages).
U.S. Notice of Allowance on U.S. Appl. No. 15/400,117 dated Jun. 15, 2017 (9 pages).
U.S. Notice of Allowance on U.S. Appl. No. 15/647,143 dated Oct. 12, 2017 (9 pages).
Upton, R. N. et al., "Pharmacokinetics and pharmacodynamics of the short-acting sedative CNS 7056 in sheep," British Journal of Anaesthesia, (2010), 105(6):798-809.
Upton, R. N., et al., "A dose escalation study in sheep of the effects of the benzodiazepine CNS 7056 on sedation, the EEG and the respiratory and cardiovascular systems," British Journal of Pharmacology, (2008) 155(1):52-61.
Upton, R.N., et al., "Comparison of the sedative properties of CNS 7056, midazolam, and propofol in sheep," Br. J. Anaesth., (2009), 103(6):848-857.
Vahabzadeh, Babac, et al., "Validation of the Prague C & M criteria for the endoscopic grading of Barrett's esophagus by gastroenterology trainees: a multicenter study." *Gastrointestinal endoscopy* 75.2 (2012): 236-241.
Walser, Armin et al., "Quinazolines and 1,4-benzodiazepines. LIX. Preparation of pyrrolo '2,1-c-1,4-benzodiazepines", J. Org. Chem., vol. 38, No. 20, (1973), pp. 3502-3507.
Wiltshire, H. R. et al., "A placebo- and midazolam-Controlled Phase I Single Ascending-Dose Study Evaluating the Safety, Pharmacokinetics, and Pharmacodynamics of Remimazolam (CNS 7056): Part II. Population Pharmacokinetic and PharmacodynamicModeling and Simulation," Anesthesia & Analgesia, (2012), 115(2):284-296.
Worthington et al., S1399: "A Phase IB Study of the Safety and Efficacy of Multiple Doses of CNS 7056 in Volunteers Undergoing Colonoscopy, Including Reversal with Flumazenil," Gastrointestinal Endoscopy, vol. 71, Issue 5, Apr. 2010, pp. AB151.
Zhao, M. et al., "Oxidation of Primary Alcohols to Carboxylic Acids with Sodium Chlorite Catalyzed by TEMPO and Bleach," Journal of Organic Chemistry, vol. 64, pp. 2564-2566 (1999).

\* cited by examiner

Figure 1

A

| Study CNS 7056-002 | | |
|---|---|---|
| Cohort Intitial dose | Success rate n/N (%) | Reasons for failure |
| Cohort 1 0.04 mg/kg | 10/15 (66.7%) | Insufficient sedation (n=5) |
| Cohort 2 0.075 mg/kg | 15/15 (100%) | No failures |
| Cohort 3 0.10 mg/kg | 9/14* (64.3%) | Insufficient sedation (n=4) Adverse event* (n=1) |

B

| Study CNS 7056-003 | | |
|---|---|---|
| Drug Dose | Success rate n/N (%) | |
| CNS 7056 0.10 mg/kg | 8/25 (32.7%) | |
| CNS 7056 0.15 mg/kg | 14/25 (56.0%) | |
| CNS 7056 0.20 mg/kg | 16/25 (64.0) | |
| Midazolam 0.075 mg/kg | 11/25 (44.0%) | |

DOSING REGIMEN FOR SEDATION WITH CNS 7056 (REMIMAZOLAM)

CROSS REFERENCE TO RELATED APPLICATIONS

This application is a continuation of U.S. application Ser. No. 16/039,198, filed on Jul. 18, 2018 and issued as U.S. Pat. No. 10,195,210, which is a continuation of U.S. application Ser. No. 15/792,636, filed on Oct. 24, 2017 and issued as U.S. Pat. No. 10,052,334, which is a continuation of U.S. application Ser. No. 15/647,143 filed on Jul. 11, 2017 and issued as U.S. Pat. No. 9,827,251, which is a continuation of U.S. application Ser. No. 15/400,117 filed on Jan. 6, 2017 and issued as U.S. Pat. No. 9,737,547, which is a continuation of U.S. patent application Ser. No. 13/883,935 and issued as U.S. Pat. No. 9,561,236, having a 371(c) date of Sep. 10, 2013, which is a 35 U.S.C. 371 national stage filing of International Application No. PCT/EP2011/005581, filed on Nov. 7, 2011, which claims priority to the following European Patent Applications: Serial No. 10 014 366.8, filed on Nov. 8, 2010; Serial No. 10 014 784.2, filed on Nov. 19, 2010; Serial No. 10 014 819.6, filed on Nov. 22, 2010; and Ser. No. 10/014,972.3, filed on Nov. 25, 2010. The contents of the aforementioned applications are hereby incorporated by reference in their entireties.

BACKGROUND OF THE INVENTION

The invention relates to a dosing regimen for sedation with the benzodiazepine 3-[(4S)-8-bromo-1-methyl-6-(2-pyridinyl)-4H-imidazo[1,2-a][1,4]benzodiazepin-4-yl] propionic methyl ester (CNS 7056; Remimazolam) in combination with an opioid, in particular fentanyl.

Sedation is a medical procedure involving the administration of sedative drugs to facilitate or enable a therapeutic or diagnostic procedure on a living subject. Sedation represents a hallmark of modern medicine and is widely used with its application ranging from minor surgery or diagnostic procedures up to ventilation of patients in intensive care units. Several classes of sedatives are known; among them benzodiazepines, which are often used and administered in combination with opioids. This combination represents the current gold standard for sedation.

The identification of an optimal dose and dosing regimen represents the most critical point when using sedatives. This is due to the high variability of blood concentrations together with high inter-individual differences in response to sedative drugs. Hence, the clinician can expect the range of individual patient response to vary between three- to fivefold for any particular sedative or analgesic agent.

Because of this variable response, the generally recommended procedure for a clinician attempting to achieve optimal sedation is to administer an initial bolus and then titrate the drug to the patient by incremental dosing until the desired level of sedation is achieved. The resulting dosing regimen which defines the initial and subsequent top-up doses and the time interval between the doses has to consider the drug's particular pharmacokinetic and pharmacodynamic properties, and has to be specifically adopted to the utilized sedative compound. Finally, the route of administration has to be defined (e.g. intravenous, oral, rectal, intramuscular, etc.).

Finding a suitable dosing regimen is particularly challenging if the sedative is used in combination with an opioid for the induction and maintenance of adequate sedation. At first, benzodiazepines and opioids interact with regard to the induction of sedation. Therefore, the administration of an opioid can reduce the amount of a benzodiazepine needed to achieve the desired level of sedation. Furthermore, benzodiazepines and opioids have additive or even synergistic effects with respect to their side effects, which increase the risk of adverse events, including hypotension, ventilatory depression and resultant hypoxemia.

As a consequence, a fixed combination of sedative and analgesic agents usually is considered to not allow the individual components of sedation/analgesia to be appropriately titrated to meet individual requirements of the patient and procedure, while reducing the associated risks, but rather maximum doses are recommended for the combination.

Recently, a new class of benzodiazepines was developed and disclosed in EP 1 183 243 B1. This class of benzodiazepines represent potent sedatives which are rapidly metabolized by tissue esterases to an inactive metabolite and thus were classified as ultra-short-active benzodiazepines.

The compound 3-[(4S)-8-bromo-1-methyl-6-(2-pyridinyl)-4H-imidazo[1,2-a][1,4]benzodiaze-pin-4-yl] propionic methyl ester (hereinafter "CNS 7056") represents one of these ultra-short-acting benzodiazepines (disclosed as example Ic-8 of EP 1 183 243 B1). CNS7056 was tested in clinical Phase I and Phase II studies with and without combination with fentanyl for producing sedation for endoscopy or colonoscopy, wherein CNS 7056 was given as body-weight adjusted dose. In these studies (CNS 7056-001, CNS 7056-002 and CNS 7056-003) CNS 7056 exhibited a fast-onset, short duration of action and rapid recovery profile.

In these studies, however, also certain deficiencies or risks with regard to the suitability of the sedation profile and tolerability became apparent. In CNS 7056-002, which was a multiple dose study, individual MOAA/S scores indicated a drop of levels to loss of consciousness (LoC) in most subjects at some point in time after the initial and/or top up doses.

Furthermore, the sedative effect exhibited significant variability. A few subjects were classified as "dropouts" (subjects who never had a MOAA/S score below or equal three despite two top-up doses) and at the same time one subject was classified as failure (underwent colonoscopy but reached full alertness, i.e. having a MOAA/S score of five).

In some cases mild hypoxic events were observed under room air conditions.

In some cases hypotension was observed when CNS 7056 was co-administered with fentanyl. Hypotension is one of the known side effects of fentanyl. However, since hypotension is also known to occur after high doses of benzodiazepines, a potential augmentation of the fentanyl-induced hypotension effect by CNS 7056 has to be considered.

Thus, an optimised dosing regimen for CNS 7056 is required.

BRIEF SUMMARY OF THE INVENTION

It is thus the objective of the present invention to provide a convenient and safe dosing regimen for the ultra-short-acting benzodiazepine CNS 7056 which also results in an improved sedation profile.

This objective is solved by the use of 3-[(4S)-8-bromo-1-methyl-6-(2-pyridinyl)-4H-imidazo[1,2-a][1,4]benzodiazepin-4-yl] propionic methyl ester (CNS 7056), according to formula (I)

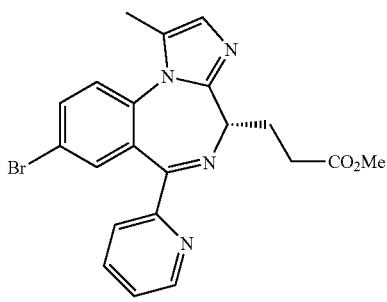

(I)

or pharmaceutically acceptable salt or solvate thereof for the induction and/or maintenance of sedation, whereby CNS 7056 is administered in combination with an opioid wherein an initial dose of CNS 7056 is 2 to 10 mg.

The dosing regimen of the invention is advantageous in terms of minimising the rate of "drop-out" subjects with MOAA/S scores of zero as well as the rate of "failures" (subjects whose sedation was not maintained satisfactorily for 60 minutes, preferably for 45 minutes and most preferably for 30 minutes with 6 top-up doses).

Furthermore the dosing regimen of the invention has considerable pharmacoeconomical advantages, because due to the rapid recovery of the patients (a short wake up time to fully alertness) the patients can be released rapidly. The time from last injection of CNS7056 until the patients are ready for discharge can be considerably shorten compared with the sedation with midazolam.

Definitions

The term "sedation" refers to a relaxed, calm state of the body and mind which is induced pharmacologically, e.g. by the use of sedatives. This also encompasses "analgosedation" which includes the concomitant application of an analgesic drug. Furthermore, as defined herein, the term sedation includes also deep sedation, preoperative sedation, anxiolysis, and anmestic use for perioperative events, conscious sedation during short diagnostic, operative or endoscopic procedures, and sedation prior and/or concomitant to the administration of other anaesthetic or analgesic agents.

The phrase "treated or administered in combination" as used herein for the combined therapeutic use or administration of CNS 7056 and an opioid (e.g. fentanyl) means that at least one dose of CNS 7056 and at least one dose of an opioid is given within a time frame, where both substances exhibit a pharmacological effect. This time frame is preferably not longer than 10 min, more preferred not longer than 8, 5, or 3 min. In one embodiment the time frame is less than 2 min. The opioid and CNS 7056 may be administered concomitantly or sequentially. This phrase encompasses treatments in which CNS 7056 and the opioid are administered either by the same route or different routes of administration.

The term "analgesia" as used herein refers to the pharmacologically induced absence or deadening of the sense of pain, e.g. by the use of analgesics, such as opioids.

The term "fixed dose" as used in the present invention relates to an amount of a drug given to a patient irrespective of his body weight.

As used herein the term "initial dose" is synonymous to the term "loading dose" and is defined as the first dose of a drug given in the context of a medical sedative treatment.

The term "top-up dose" relates to a dose given after the initial dose or a previous top-up dose in the context of a medical treatment.

The term "minimal sedation" or "mild sedation" refers to a drug-induced state during which the patient responds normally to verbal commands. Cognitive function and coordination may be impaired. Ventilatory and cardiovascular functions are unaffected. Minimal sedation is also known as anxiolysis.

The term "moderate sedation" (synonymously with conscious sedation) refers to a drug-induced depression of consciousness during which the patient responds purposefully to verbal command, either alone or accompanied by light tactile stimulation. No interventions are necessary to maintain a patient airway. During moderate sedation spontaneous ventilation is adequate and the cardiovascular function is usually maintained.

The term "deep sedation" refers to a drug-induced depression of consciousness during which the patient cannot be easily aroused, but responds purposefully following repeated or painful stimulation. Independent ventilatory function may be impaired. The patient may require assistance to maintain a patient airway. During deep sedation the spontaneous ventilation may be inadequate and cardiovascular function is usually maintained.

The term "procedural sedation" refers to a technique of administering sedatives or dissociative agents with or without analgesics to induce a state that allows the patient to tolerate unpleasant procedures while maintaining cardio respiratory function. Procedural sedation and analgesia is intended to result in a depressed level of consciousness that allows the patient to maintain oxygenation and airway control independently.

The term "analgosedation" refers to a pharmacologically induced analgesia with concurrent sedation. In contrast to the anaesthesia the patient can react on external stimuli and breathe unaided. Dependent on the dose of the sedative and/or the analgesic drug the analgosedation can, intentionally or not, reach the state of general anaesthesia.

The term "general anesthesia" refers to a drug-induced loss of consciousness (LoC) during which the patient is not arousable, even to painful stimuli. During general anesthesia the ability to maintain independent ventilatory function is often impaired and assistance is often required in maintaining a patient airway. Furthermore, positive pressure ventilation may be required due to depressed spontaneous ventilation or drug-induced depression of neuromuscular function and cardiovascular function may be impaired.

The term "monitored anesthesia care" as used herein refers to a specific anesthesia service for a diagnostic or therapeutic procedure which includes the following aspects of anesthesia care: (i) a preprocedure visit, (ii) intraprocedure care, and (iii) postprocedure anesthesia management. During monitored anesthesia care, the anesthesiologist provides or medically directs a number of specific services, including but not limited to diagnosis and treatment of clinical problems that occur during the procedure, support of vital functions, administration of sedatives, analgesics, hypnotics, anaesthetic agents or other medications as necessary for patient safety, psychological support and physical comfort, and provision of other medical services as needed to complete the procedure safely.

Monitored anesthesia care may include varying levels of sedation, analgesia, and anxiolysis as necessary. The provider of monitored anesthesia care must be prepared and qualified to convert to general anesthesia when necessary. This is the case, when the patient loses consciousness and the ability to respond purposefully, irrespective of whether airway instrumentation is required.

For assessment of the various states of sedation and analgosedation the so called Modified Observer's Assessment of Alertness and Sedation scale (MOAA/S) and, alternatively, the Ramsey Scale often are used. These scales are as follows:

| Modified Observer's Assessment of Alertness/Sedation Scale | |
| --- | --- |
| Responsiveness | Score |
| Agitated | 6 |
| Responds readily to name spoken in normal tone (alert) | 5 |
| Lethargic response to name spoken in normal tone | 4 |
| Responds only after name is called loudly and/or repeatedly | 3 |
| Responds only after mild prodding or shaking | 2 |
| Does not respond to mild prodding or shaking | 1 |
| Does not respond to deep stimulus | 0 |

| Ramsey Sedation Scale | |
| --- | --- |
| Responsiveness | Score |
| Patient is anxious and agitated or restless, or both | 1 |
| Patient is cooperative, oriented and tranquil | 2 |
| Patient responds to commands only | 3 |
| Patient exhibits brisk response to light glabellar tap or loud auditory stimulus | 4 |
| Patient exhibits a sluggish response to light glabellar tap or loud auditory stimulus | 5 |
| Patient exhibits no response | 6 |

The term "opioid" which is synonymous to the term "opioid drug" as used herein refers to compounds which have the same mode of action as the constituents of opium, the dried milky liquid of the poppy seed, *Papaver somniferum*. All opioid drugs interact in biological systems with the same type of receptor, the so called opioid receptor. According to the analgesia and side effect profile five types of opioid receptors, the μ-receptor (ligand=morphine), the κ[kappa]-receptor (ligand=ketazocine), the delta-receptor (ligand=deltorphine II), the o[sigma]-receptor (ligand=SKF 10081), as well as the later-identified ORL1-receptor (ligand=nociceptin) are known. Corresponding to other receptor systems, binding studies as well as functional investigations indicate that subtypes of opioid receptors exist. Within the μ- and δ-receptor type 2 subtypes, the μ-1 and μ-2 and δ-1 and δ-2 have been described. The κ-receptor contains an additional κ-3 subtype. Especially in regards to the μ-opioid receptor its two subtypes are included in this invention.

The term "endoscopy" refers to techniques used to inspect or to look into internal cavities or hollow structures of an organism.

The term "upper GI endoscopy" refers to an examination of the inside of the upper gastrointestinal tract such as the oesophagus, stomach and/or duodenum. It is typically performed by using a thin, flexible fibre-optic instrument that is passed through the mouth and allows the observation of the lining of the oesophagus stomach and/or duodenum. It is also referred as esophagogastroduodenoscopy (EGD) or gastroscopy. The upper GI endoscopy also includes other GI procedures such as the endoscopic retrograde cholangiopancreaticography (ERCP).

As used herein the term "colonoscopy" refers to an endoscopic examination of the rectum and colon up to the ileocaecal valve. Typically, this procedure is performed with a CCD camera or a fibre optic camera on a flexible tube passed through the anus.

The term "amnestic use" as used herein relates to the induction of amnesia, which represents the partial or total loss of memory.

The term "operative procedure" as used herein refers to all kind of medical intervention into the living body, either invasive or non-invasive, for diagnostic and/or therapeutic purposes. Medical intervention in particular comprises medical treatments which, on a regular basis, are expected to cause post-operative pain for the patient. As a synonymous term for "operative procedure" the term "surgery" is also used herein.

Manual or mechanical ventilation is defined as external assistance in breathing by manual or mechanical methods such as e.g. mask ventilation, or intubation.

The phrase "pharmaceutically acceptable salt" refers to a salt of variable stoichiometry formed by compound of formula (I) and a counter ion and which is physiologically tolerable and/or do not typically produce an allergic or similar untoward reaction, such as gastric upset, dizziness and the like, when administered to a mammal.

As used herein, the term "solvate" refers to a complex of variable stoichiometry formed by a solute (in this invention, a compound of formula (I), an opioid or a salt thereof) and a solvent. Such solvents for the purpose of the invention may not interfere with the biological activity of the solute. Examples of suitable solvents include, but are not limited to water, methanol, ethanol and acetic acid. Preferably the solvent used is a pharmaceutically acceptable solvent Examples of suitable pharmaceutically acceptable solvents include water, ethanol and acetic acid. Most preferably the solvent used is water.

DETAILED DESCRIPTION OF THE INVENTION

The invention relates to the ultra-short-acting benzodiazepine CNS 7056 or a pharmaceutically acceptable salt or solvate thereof for induction of sedation, whereas CNS 7056 is administered in combination with an opioid. Preferably both drugs are given intravenously. Moreover, both drugs are preferably administered in a fixed dose. The dose of CNS 7056 can vary between about 2 to about 10 mg, preferably between about 3 (or 4) mg and about 9 mg, and most preferably between about 5 and about 8 mg. In a particular embodiment of the invention 10 mg CNS7056 is administered.

Thus, it has been found out that a fixed dose determined from the putative drug exposure and clearance provides a safe and effective dose, especially in the context of the above claimed dosing regimen.

In one embodiment of the invention CNS7056 is administered as a bolus injection with a concentration of CNS 7056 of 1 mg/ml.

In a preferred embodiment of the invention at least one further top-up dose of CNS 7056 follows the initial dose of CNS 7056. The top-up dose is between around 1.5 and around 4 mg, preferably between around 2 and around 3, and most preferably 2 or 3 mg.

In a preferred aspect of the invention, CNS 7056 is administered in a fixed dose, whereas the initial dose and the top-up doses are combined as follows:
8 mg initial dose plus 2 or 3 mg top-up dose, or
7 mg initial dose plus 2 or 3 mg top-up dose, or
5 mg initial dose plus 2 or 3 mg top-up dose 4 mg initial dose plus 2 or 3 mg top-up dose or
3 mg initial dose plus 2 or 3 mg top-up dose.

In a particular embodiment the initial dose and the top-up(s) are selected to provide a maximum dose of 10 mg per treatment.

In a further preferred aspect of the invention, CNS 7056 is administered in a fixed dose, whereas the initial dose and the top-up doses are combined as follows:
8 mg initial dose plus 3 mg top-up dose, or
7 mg initial dose plus 2 mg top-up dose, or
5 mg initial dose plus 3 mg top-up dose.

In one aspect of the invention the patients receive an initial single intravenous dose of CNS 7056 over one minute.

In another aspect of the invention the CNS 7056 top-up dose is administered not less than 2, preferably 3 minutes and more preferably 4 minutes apart from the starting or the previous top up dose.

In one aspect of the invention up to a maximum of six top-up doses of CNS 7056 are given, so that not more than seven doses of CNS 7056 are given per treatment. However, it was found out by the inventors that with an initial dose of up to 10 mg—if at all—only 1 to 3, preferably not more than 2, top up doses are needed. Thus in one aspect of the invention the number of top ups is below 3, preferably even below 2.

The medical treatment—and thus the required sedation according to the invention—preferably lasts less than one hour, preferably less than 45 minutes and more preferably less than 30 minutes.

According to the invention the top-up doses can contain the identical or a different amount of CNS 7056, whereas the use of identical amounts of CNS 7056 is preferred.

In another aspect of the invention the dosing regimen is adjusted in order to maintain a MOAA/S score of not more than 4 (including 4), preferably of 1 to 4, and more preferably of 2 to 4. This adjustment is preferably performed by alteration of the top-up doses with regard to the dose of the top-up dose or the time interval between the top-up doses or both. In a further preferred aspect of the invention a change in the time interval between the top-up doses is used for maintaining the level of the MOAA/S score. Hereby, the time interval is shortened in case that the patient exhibits reduced sedation and prolonged in case of increased sedation.

In a further aspect of the invention the dosing regimen is adjusted in order to induce and/or maintain a mild to moderate sedation, which may be assessed by the MOAA/S and categorized by the following scheme:

| Level of sedation | MOAA/S score |
| --- | --- |
| Fully alert | 5 |
| Mild sedation | 4 |
| Moderate sedation | 2-3 |
| Deep sedation | 0-1 |
| Loss of consciousness | 0 |

In one embodiment the sedation profile of the invention is preferably characterized by:
MOAA/S≤4 at three consecutive measurements, e.g. taken every minute
no requirement for a further sedative (e.g. a rescue sedative)
no manual or mechanical ventilation Hence in one embodiment the invention relates to the use of CNS7056 in combination with an opioid (e.g. fentanyl) without a mechanical or manual ventilation of the patient. Nevertheless supplemental oxygen supply is possible.

In a further aspect of the invention CNS 7056 is administered as a fixed dose per patient. This dosing strategy is based on an extensive PK/PD analysis which revealed that the body weight was not a statistically significant predictor of the systemic clearance or exposure of CNS 7056 and so dosing in units of mg/kg offers no advantage in terms of safety or efficacy.

In another aspect of the invention CNS 7056 is given to adult patients, i.e. which are 18 years or older.

Methods for preparation of CNS 7056 together with pharmaceutically acceptable forms are described in EP application EP 1 183 243 B1. Suitable forms for use in pharmaceutical compositions are also described therein. This document is incorporated by reference as to the disclosure of the manufacture of pharmaceutically acceptable forms of CNS 7056.

The compound CNS 7056 can be used as free base form or as a pharmaceutically acceptable salt. As a preferred salt the besylate or esylate salt of CNS 7056 can be used. The besylate and esylate salts of CNS 7056 are described by the PCT applications WO 2008/007071 and WO 2008/007081, respectively. These salts as disclosed therein are incorporated by reference.

In a further preferred aspect of the invention the besylate salt of CNS 7056 is used in one of the polymorphic salt forms 1, 2, 3 or 4 as described by PCT application WO 2008/007071. These polymorphic forms as disclosed therein are fully incorporated by reference.

In another aspect of the invention the esylate salt of CNS 7056 is used in the polymorphic salt form 1 or 2 as described by PCT application WO 2008/007081. These polymorphic forma as disclosed therein are fully incorporated by reference.

According to the invention the ultra short-acting benzodiazepine CNS 7056 is administered as an intravenous (IV) bolus application, preferably as IV bolus of less than 1 minute, more preferably less than 30 seconds and most preferably of approximately 15 seconds, which is equivalent to a manual application of an intravenous drug.

In one aspect of the invention the opioid drug is preferably selected from the group consisting of:
morphine, codeine, thebain, papaverin, narcotine, heroin, hydromorphone, dihydrocodeine, thebacon, hydrocodone, oxymorphone, oxycodone, ketobemidone, pethidine, anileridine, piminodine, phenoperidine, furethidine, [alpha]-prodin, trimeperidine, meptazinol, profadol, methadone, dextromoramide, levomethadyl acetate, phenadoxone, dipipanone, themalon, dextropropoxyphene, N-methylmorphinan, levorphanol, dextrometorphane, butorphanol, pentazocine, phenazocine, ketocyclazocine, bremazocine, sufentanil, carfentanil, fentanyl, lofentanil, alfentanil, ohmefentanil, remifentanil, pitramide, benztriamide, diphenoxylate, loperamide, tramadol, tilidine, U-50488, 1-benzyl-4-(4-bromo-phenyl)-4-dimethylamino-cyclohexanol;
alfentanil, buprenorphine, butorphanol, codeine, dextromoramide, dextropropoxyphene, dezocine, diamorphine, dihydrocodeine, diphenoxylate, ethylmorphine, etorphine, hydrocodone, hydromorphone, ketobemidone, levomethadone, levomethadyl-acetate, levorphanol, meptazinol, morphine, nalbuphine, nalorphine, oxycodone, oxymorphone, pentazocine, pethidine, piritramide, remifentanil, sufentanil, tilidine, tramadol, tapentadol, met-enkephalin, leu-enkephalin, nociceptin, ß-endorphin, endomorphin-1, endomorphin-2, metorphamid, dynorphin-A, dynorphin-B, or α-neoendorphin.

The analgesic drug is administered preferably as an intravenous bolus application.

In a more preferred aspect of the invention the patient is given a fentanyl analogue according to formula (II):

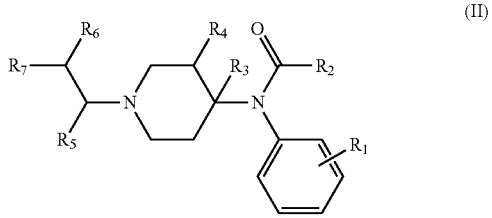

wherein
$R_1$ is H, F, Cl, Br, or J;
$R_2$ is $C_1$-$C_4$ alkyl;
$R_3$ is H, $CH_2$—O—$(CH_2)_n$—$CH_3$ with n=0-3, or $COOR_8$ with $R_8$=$C_1$-$C_4$ alkyl;
$R_4$ is H, $C_1$-$C_4$ alkyl;
$R_5$ is H, —OH, $C_1$-$C_4$ alkyl;
$R_6$ is H, —OH;
$R_7$ is Aryl, heteroaryl or $COOR_8$.

In a most preferred aspect of the invention the patient is given a fentanyl analogue selected from the group consisting of fentanyl, alfentanil, carfentanil, lofentanil, remifentanil, sufentanil, thiofentanyl, α-methylthiofentanyl, α-methylacetylfentanyl, α-methylfentanyl, ohmefentanyl, ß-hydroxy-fentanyl, parafluorfentanyl, 3-methylfentanyl or a salt or a solvate thereof.

These fentanyl analogues are defined by a structure of formula (II) wherein the residues $R_1$ to $R_7$ are given as follows:

| Substance | $R_1$ | $R_2$ | $R_3$ | $R_4$ | $R_5$ | $R_6$ | $R_7$ |
|---|---|---|---|---|---|---|---|
| fentanyl | —H | —$CH_2CH_3$ | —H | —H | —H | —H | -phenyl |
| alfentanil | —H | —$CH_2CH_3$ | —$CH_2OCH_3$ | —H | —H | —H | 4-ethyl-5-oxo-1,4-dihydrotetrazol-1-yl |
| carfentanil | —H | —$CH_2CH_3$ | —$COOCH_3$ | —H | —H | —H | -phenyl |
| lofentanil | —H | —$CH_2CH_3$ | —$COOCH_3$ | —$CH_3$ | —H | —H | -phenyl |
| remifentanil | —H | —$CH_2CH_3$ | —$COOCH_3$ | —H | —H | —H | —$COOCH_3$ |
| sufentanil | —H | —$CH_2CH_3$ | —$CH_2OCH_3$ | —H | —H | —H | 2-thienyl |
| thiofentanyl | —H | —$CH_2CH_3$ | —H | —H | —H | —H | 2-thienyl |
| α-methylthio-fentanyl | —H | —$CH_2CH_3$ | —H | —H | —$CH_3$ | —H | 2-thienyl |
| α-methyl-acetylfentanyl | —H | —$CH_3$ | —H | —H | —$CH_3$ | —H | -phenyl |
| α-methylfentanyl | —H | —$CH_2CH_3$ | —H | —H | —$CH_3$ | —H | -phenyl |
| ohmefentanyl | —H | —$CH_2CH_3$ | —H | —$CH_3$ | —$CH_3$ | —OH | -phenyl |
| β-hydroxyfentanyl | —H | —$CH_2CH_3$ | —H | —H | —H | —OH | -phenyl |
| parafluorfentanyl | p-F | —$CH_2CH_3$ | —H | —H | —H | —H | -phenyl |
| 3-methylfentanyl | —H | —$CH_2CH_3$ | —H | —$CH_3$ | —H | —H | -phenyl |

In a particular preferred aspect of the invention the patient is given fentanyl or a pharmaceutically acceptable salt or solvate thereof.

The results of the PK/PD analysis revealed a pharmacodynamic interaction between fentanyl and CNS 7056 when the application of fentanyl was within 5 to 10 minutes prior to the initial administration of CNS 7056. This interaction between fentanyl is also supported by the results of the clinical study CNS 7056-002, in which CNS 7056 was applied in combination with fentanyl, as in this study lower doses of CNS 7056 led to a suitable sedation as compared to the studies CNS 7056-001 and CNS 7056-003, in which CNS 7056 was applied as a single agent (see FIG. 1A versus FIG. 1B). The doses which led to sufficient sedation to perform the procedure (i.e. MOAA/S below or equal 4) in study CNS 7056-002 in 64 to 100% of subjects ranged from 0.04 mg/kg to 0.1 mg/kg of CNS 7056 plus top up doses of 0.04 mg/kg in addition to 50 mcg of fentanyl in order to keep the sedation for a period of 30 minutes. In study CNS 7056-003 single doses of CNS 7056 of 0.1 mg/kg to 0.2 mg/kg without concomitant fentanyl led to sufficient sedation in 32-64% of patients. This supports a safe use of fentanyl in combination with CNS7056.

A sufficient analgesic coverage as provided by fentanyl reduces also the requirement of top-up doses of CNS 7056, resulting in a more stable situation for mild to moderate sedation and avoiding frequent drops to MOAA/S levels of 0.

In one aspect of the invention the fentanyl that is given in a fixed dose regimen, is preferably between 50 to 200 mcg/patient, more preferably between 75 and 150 mcg/patient and most preferably 100 mcg/patient.

As mentioned above the results of the PK/PD analysis found no evidence for a pharmacodynamic interaction between fentanyl and CNS 7056. This lack of PD interaction allows administration of fentanyl in a broad dose range, as claimed herein. This rather high dose of fentanyl, especially when given shortly before the start of the diagnostic or therapeutic intervention, results in a maximum analgesic coverage at the start of the diagnostic or therapeutic intervention.

In a most preferred aspect of the invention, 100 mcg of fentanyl is given immediately before or together with the initial fixed dose of CNS 7056.

In a further aspect of the invention the fentanyl is administered not earlier than 10 minutes before administration of CNS 7056, preferably within at least 5 minutes prior to CNS 7056 administration, more preferably within at least 3 minutes prior to CNS 7056 administration and most preferably together with CNS 7056.

The short time interval between fentanyl dosing and CNS 7056 results in a maximum analgesic coverage at the start of the diagnostic or therapeutic intervention. This is important for procedures that start with painful interventions. As an example in colonoscopy the insertion of the scope and its movement through the sigmoid curve of the colon at the beginning is the most inconvenient and painful part of the procedure.

In one aspect of the invention at least one additional (top-up) dose of fentanyl is given, preferably in the range of 10 to 100 mcg/patient, more preferably in the range of 10 to 75 mcg/patient and most preferably 25 mcg/patient.

In a further aspect of the invention the time interval between the first fentanyl dose and the top-up dose and/or between two top-up doses is in the range between 2 to 10 minutes, In another aspect of the invention CNS 7056 is used for preoperative sedation, anmestic use for perioperative events, or conscious sedation during short diagnostic, operative or endoscopic procedures.

In another aspect of the invention CNS7056 as of the invention is used for short procedures such as limb resetting or wound dressing.

In a preferred aspect of the invention CNS 7056 is used for analgosedation.

In another aspect of the invention the use of CNS 7056 is contraindicated for subjects with known hypersensitivity to benzodiazepines and subjects with acute narrow-angle glaucoma. CNS 7056 may be used in patients with open-angle glaucoma only if they are receiving appropriate therapy.

In another embodiment the invention CNS7056 is provided in a container for pharmaceutical use comprising 10 mg of CNS7056, preferably in a concentration of 1 mg/ml, e.g. a vial, ampoule, syringe or the like. The container comprising 10 mg CNS7056 preferably constitutes a drug product, preferably a ready-to-use drug product.

In a further aspect of the invention the pharmacological effect of the ultra short-acting benzodiazepine CNS 7056 and/or the opioid drug can be reversed by another drug, which is referred to as a "reversal agent".

As reversal drug for the ultra short-acting benzodiazepine CNS 7056 a GABA receptor antagonist is used, which is preferably flumenazil.

As reversal drug for the opioid drug an opioid receptor antagonist is used, preferably naloxone.

Example 1

The principal objectives of the analysis were to fit pharmacokinetic and pharmacodynamic (especially Modified Observer's Assessment of Alertness/Sedation (MOAA/S) scores) models to the data obtained from the studies CNS 7056-001 and CNS 7056-002 and use the parameters obtained to simulate the results of different dosing regimens in order to predict an optimal dose regimen for CNS 7056. Secondary objective was to explore the pharmacodynamic interaction between CNS 7056 and fentanyl during Study CNS 7056-002.

Materials and Methods

Study CNS 7056-001

Pharmacokinetic data were obtained after CNS 7056 had been administered by intravenous infusion over one minute to groups of healthy volunteers at the following doses: 0.01, 0.025, 0.05, 0.075, 0.1, 0.15, 0.2, 0.25 and 0.3 mg/kg. Both arterial (1, 2, 3, 4, 6, 8, 10, 12, 15, 20, 30, 45 minutes and 1, 2, 3, 4 hours post-dose) and venous (2, 3, 4, 6, 8, 12 hours) blood samples containing CNS 7056 and its metabolite, CNS 7054, were obtained from indwelling catheters. Concentrations of CNS 7056 and CNS 7054 were measured using HPLC with tandem mass spectrometric detection. Measurements of sedation (MOAA/S and Bispectral Index (BIS) scores) and systolic and diastolic blood pressure were made at regular intervals.

Study CNS 7056-002

In the second part of the study, all subjects received a 50 mcg intravenous dose of fentanyl followed by a further 25 mcg if the initial pain relief was inadequate. Three cohorts of 15 patients were given loading doses of CNS 7056 at 0.04, 0.075 or 0.1 mg/kg with the higher doses only being administered once the safety of the lower doses had been assessed. Up to a maximum of two supplemental, 0.04 mg/kg doses of CNS 7056 were administered, not less than two minutes apart to obtain adequate sedation (MOAA/S≤3) for insertion of the colonoscope. Further 0.04 mg/kg doses of CNS 7056 were administered during the procedure, no earlier than two minutes after the previous dose, in order to maintain a MOAA/S level of ≤4 for 30 minutes; no more than seven doses (the initial and six top-up doses) could be administered to any subject. The gender ratio in each cohort was 7:8. Venous plasma levels of CNS 7056 were measured at 1, 5, 10, 20 and 30 minutes and at 1, 2, 4, 6, 8, 12 and 24 hours post-dose.

Analysis

Physiologically-based three- and four-compartment pharmacokinetic models were fitted to the arterial and venous plasma levels of CNS 7056 from the combined data obtained in Studies CNS 7056-001 and CNS 7056-002 using the non-linear modelling programme, NONMEM. The possible influence of body weight, sex and heart rate on volumes and clearances was examined by covariate analysis. The derived pharmacokinetic parameters from the preferred models were then used to simulate the arterial concentrations of the drug at the time points at which pharmacodynamic data, MOAA/S scores and blood pressures, were obtained and sigmoid inhibitory pharmacodynamic models fitted to the observations via a "link" model, again using NONMEM. A number of sudden, apparently random, increases in MOAA/S score of short duration were identified within the data-set and attributed to external stimuli such as acute pain from the colonoscope or treatment by the nursing staff; these were modelled by the introduction of a covariate which increased EC50. Another covariate, the "scoping-factor" which also increased EC50, was added to the model in order to simulate reduced sedation during the actual colonoscopy procedure caused by general irritation. As no concentrations of fentanyl were obtained during Study CNS 7056-002, historical values of clearances and volumes of distribution were used in order to simulate plasma levels of the opioid so that pharmacodynamic models of hypotension and interaction with CNS 7056 could be developed. The interaction model of sedation introduced a covariate, estimated by the modelling, which converted simulated plasma levels of fentanyl into concentrations of CNS 7056 at the effect site.

Population Pharmacokinetic Analysis

A sequential population approach was employed, first estimating the pharmacokinetic parameters for CNS 7056 and then using these results to obtain the corresponding pharmacodynamic parameters. A non-linear, mixed-effect modelling programme (NONMEM, version 6) was applied to the data using the first order conditional estimation with interaction method (FOCE-I). Physiologically-based pharmacokinetic models were fitted to a combination of arterial and venous plasma levels of CNS 7056 from the combined CNS 7056-001 and CNS 7056-002 data sets (FIG. 2), using the ADVAN6 sub-programme, with tolerance (TOL) set to five, to solve the differential equations. All the models contained a central compartment corresponding to the venous system and other highly perfused tissues, arterial, pulmonary, peripheral and deep compartments. Clearance of CNS 7056 to CNS 7054 was assumed to take place from the central, pulmonary or peripheral compartments, or from a hepatic one (FIG. 2). A combination of two clearance compartments was also investigated. An additional "deeper" compartment was introduced as models with four-compartments had been shown to be superior to those with three in study CNS 7056-001. Since the erythrocyte penetration of CNS 7056 was not known, cardiac output of blood/plasma was estimated during the modelling process.

Results

Population Pharmacokinetic Analysis of CNS 7056

Modelling of the arterial plasma levels of CNS 7056 in Study CNS 7056-001 found that, although a three-compartment model fitted the data well, the corresponding four-compartment model, with systemic clearance from the central compartment, gave a considerably smaller objective function. In addition, when clearance was assumed to have taken place in the peripheral compartment, there was a further substantial drop in objective function.

The simplest physiologically-based pharmacokinetic models, therefore, contained three compartments of unknown volume plus arterial and pulmonary compartments whose volumes (arteries=0.65 kg/70 kg, lungs=1.0 kg/70 kg) were assumed to be proportional to body weight. Systemic clearance and the two inter-tissue clearances were also unknown. Since the erythrocyte penetration of CNS 7056 was not known, cardiac output of blood/plasma also had to be estimated during the modelling process.

This model was expanded to one with four compartments of unknown volume and the site of clearance allowed to be the central, peripheral, pulmonary or an additional hepatic compartment, whose volume (1.5 kg/70 kg) and relative blood flow (26% of cardiac output) were assumed to be those of a standard subject. Inter-individual variability (IIV or Eta) was included for systemic clearance, central, peripheral and deep volumes of distribution in all models, together with proportional and additive residual errors. A fifth Eta, on the volume of the fourth compartment, was also investigated with each model.

Of the simple, three-compartment models, that with clearance from the lung (Run 128S) was clearly the best. Among the four-compartment models with dual clearance, the Run 144S with clearance from both the lung and liver proved to be the best one in terms of lowest objective function. A comparison of the parameters from the better physiologically-based pharmacokinetic models is shown in Table 1.

Covariate Analysis of the Population Pharmacokinetic Analysis of CNS 7056

Body Weight does not Predict Clearance, Volumes or Blood Flow

Inter-individual variability on cardiac output and a limited covariate analysis was undertaken based on the three-compartment model Run 128S with pulmonary clearance of CNS 7056. When body-weight was considered as a predictor of clearance (Run 137S), volumes (Runs 130S, 152S, 153S) or blood flow (Run 127S) the objective function was essentially unchanged; in this case final minimisation did not occur (Table 2).

The absence of an influence of body-weight on the clearance of CNS 7056, shown by the insignificant change in objective function when the covariate was introduced (Run 137S, Table 2), was also demonstrated by plotting body-weight against the fitted values of pulmonary clearance, using the results of Run 128S (FIG. 3), the slope of the linear regression equaling 0.1 with an $R^2$ of 0.0155.

Conclusion:

As no relationship was found between body weight and systemic clearance (FIG. 3), there is no advantage in dosing by weight in terms of consistency of exposure to CNS 7056.

Population Pharmacodynamic Analysis

Continuous pharmacodynamic models were fitted to the MOAA/S data, even though these were categorical, because they are more stable when there are several categories and because the results are more readily interpreted. Simple sigmoid inhibition pharmaco-dynamic models fitted the MOAA/S data poorly and it was found necessary to modify the data-set in order that the observed scores could be accurately fitted. One- and two-minute "spikes" of increased MOAAS/S score were identified within the data-set and modelled as increases in $EC_{50}$ of approximately 30%. The unexpected result that the efficacy of CNS 7056, expressed as the typical $EC_{50}$, was the same in Study CNS 7056-001 (healthy volunteers) and CNS 7056-002 (patients undergoing a colonoscopy) was rationalised by assuming that residual sedation from the pre-operative dose of fentanyl was roughly nullified by general irritation throughout the procedure. A "scoping-factor", which typically caused a 10-12% increase in $EC_{50}$, was introduced to account for this.

MOAA/S Pharmacodynamic Analysis of CNS 7056

All MOAA/S data from Studies CNS 7056-001 and CNS 7056-002 were used for the pharmacodynamic modelling of sedation. Arterial plasma levels calculated from the pharmacokinetic parameters estimated previously from model CNS 7056 PBPK128S were linked to an inhibitory sigmoid effect pharmacodynamic model of sedation via a hypothetical "effect" site and a delay rate constant "ke0". $E_{MIN}$ was set to zero and $E_{MAX}$ to five for the basic MOAA/S models and IIV included for the three pharmacodynamic parameters, $EC_{50}$, ke0 and Hill coefficient, γ. Since the basic models minimised with a singular R-matrix, the control files of all subsequent MOAA/S models, were amended to include the MATRIX=S command in order that the covariance step could be performed.

The data-sets from Studies CNS 7056-001 and CNS 7056-002 were analysed separately and then after being combined (Table 3). All of the parameters were estimated with good precision (average RSE %: 5.4-7.9%) and IIV of approximately 40% for all three pharmacodynamic parameters (Table 3). There were no obvious differences between the three pharmacodynamic parameters with $EC_{50}$ and ke0 from the individual studies being within about 10% (Table 3). The combined data set "MOAASALL01S" was used for the subsequent pharmacodynamic modelling.

Covariate Analysis of Fentanyl as a Predictor of Sensitivity to CNS 7056

Although the pharmacodynamic parameters of the MOAA/S models from Studies CNS 7056-001 and CNS 7056-002 were similar, the possible effect of fentanyl, used only in the second study, was investigated (Table 4). The first model (MOAASALL05S) assumed that $EC_5$ was different in the presence of fentanyl, but the value obtained (0.338 mcg/ml) was very similar to that in its absence (0.364 mcg/ml) and the decrease in objective function compared to model MOAASALL01S, which assumed that the typical value of $EC_{50}$ was unaffected by fentanyl, was insignificant (ΔOFV=−0.85, Table 4). When the actual dose of fentanyl (0, 50, or 75 mcg) was taken into account (model MOAASALL09S), the decrease in objective function was again minimal (ΔOFV=−1.73, Table 4).

CNS 7056-Fentanyl Interaction MOAA/S Analysis

The use of covariate analysis to examine a possible pharmacodynamic interaction between fentanyl and CNS 7056 assumes a constant effect throughout the observation period. However, fentanyl was given a 5-10 minutes before CNS 7056 and, as its clearance is quite rapid, concentrations towards the end of the procedure are likely to have been relatively low. Accordingly, historical data (Table 5) were used to simulate appropriate plasma levels of fentanyl and these were assumed to be reflected as equivalent concentrations of CNS 7056 at the effect site via an equivalence parameter. The correct times of the later MOAA/S scores were used in all the models of the CNS 7056-Fentanyl interaction.

When a fentanyl effect was added to the basic model, the equivalence factor was very small and slightly negative (−4.46) and there was no significant change in objective function (Runs FEN01AS and FEN03S, Table 6). However, when allowance was made for the pain associated with colonoscopy, there was a significant decrease in objective function (Run FEN05S, ΔOFV=−67.6, Table 6) and a larger, positive concentration-equivalence factor of 21.5. In addition the effect attributed to the colonoscope in reducing sedation (i.e. increasing $EC_{50}$) rose from 11.6% to 14.5% (Runs FEN04S and FEN05S, Table 6). Allowance for inter-subject variability in the pharmacodynamic interaction further reduced the objective function by 35 (Runs FEN06S, FEN05S), although the inter-subject variability was large at 162% and poorly estimated (Table 6).

As the systemic clearances of fentanyl and CNS 7056 are comparable at roughly 60 l/h (Table 5), the relative systemic exposures are essentially proportional to the ratio of their respective doses. Thus for typical single doses of CNS 7056 and fentanyl of 7 and 0.05 mg, respectively, systemic exposure would be approximately 0.12 and 0.00083 mcg·h/ml for the two drugs. An equivalence factor of 20 would, therefore, raise the apparent exposure of fentanyl to 0.017 mcg·h/ml, 14% of that of CNS 7056.

The effects of sudden additional stimuli were introduced into the fentanyl-interaction model with similar results (Table 7) to those with the simpler model (Table 8, Table 9). Thus one and one/two minute stimuli gave rise to reductions in objective function of 237 (Run FEN07S) and 351 (Run FEN08S), respectively, compared to 253 and 371 for the simpler model (Runs MOAASALL21 and MOAASALL23, Table 8). Combining the effects of the colonoscope and additional stimuli on $EC_{50}$ also reduced the objective functions (Runs FEN09S, FEN05S: ΔOFV=363, Tables 6 and 7) in a similar manner to the simpler models (Runs MOAASALL31 and MOAASALL18: ΔOFV=−352, Table 9).

Inter-subject variability had the least effect when applied to the additional stimuli (Run FEN11S, ΔOFV=−21, Table 10) and the reductions in objective function for the concentration-equivalence factor (ΔOFV=−63, Run FEN14S) and colonoscopy parameter (ΔOFV=−73, Run FEN18S) were similar. Combinations of these two produced the preferred model, Run FEN19S with an objective function of 2053.7 compared to the best without any fentanyl effect of 2152.8 (MOAASALL32S, Table 9, ΔOFV=−99.1). A direct comparison between MOAASALL27S and Run FEN11S (OFV=2169.0) which had inter-individual variability (IIV) on the same parameters, demonstrates an improvement in objective function of 24.5 with the interaction model. As with the simpler modes, the data set was modified with the zero scores being changed to negative values. The exact correspondence of the observed and fitted scores, after rounding to integer values, was 70% for the final fentanyl-interaction model with 23% of the results differing by one. The model was further optimised in an analogous manner to the simpler model, as above, in order to maximise the correspondence of the observed and modelled zero scores (Table 11). In this case the difference between the objective functions of the corresponding models was 19 and 51, but increased to 221 by the substitution of IIV on the concentration-equivalence and scoping factors for $E_{MIN}$ (Table 12). The interaction model assumed that fentanyl concentrations at the effect site were equivalent to those of CNS 7056 after multiplication by a concentration-equivalence factor determined by the modelling. The population mean of this factor was 28 (Table 13) and ranged from 6 to 330 (Table 14). Bearing in mind that the typical loading doses of CNS 7056 were roughly 100 times those of fentanyl (total doses 3-4 times as high) and that the clearances of the two compounds are comparable, this indicates that fentanyl might contribute in the order of a quarter of the sedation of the loading doses of CNS 7056 (mean dose=5.5 mg) and 5-10% of the overall effect (mean total dose=19.4 mg).

Pharmacodynamic Analysis Using the Monte Carlo Method

Monte-Carlo simulations were undertaken using the pharmacodynamic parameters from both the preferred simple and CNS 7056-fentanyl interaction models of MOAA/S score, varying the loading and top-up doses and including a similar proportion of spikes of reduced MOAA/S score. A total of 1000 Monte Carlo simulations was carried out at a range of dosing regimens likely to be appropriate for CNS 7056 (Table 15), using the pharmacodynamic parameters from Run MOAASALLMIN61S (Table 16). The simulations generated fractional MOAA/S scores which were rounded to the nearest integer, negative numbers being considered to be zero. The results of the modelling automatically assumed that all patients were treated in the same way as those of Studies CNS 7056-001 and CNS 7056-002 (i.e. no-fentanyl-no-colonoscopy or fentanyl (50 mcg or 75 mcg 5-10 minutes before CNS 7056) plus colonoscopy). The following protocol was followed:

Initial doses of CNS 7056 had to be sufficient to give adequate sedation (MOAA/S Score of three or lower) to most subjects so that the colonoscope could be inserted.

One or two top-up doses were allowed if the MOAA/S scores were still above three. If these were insufficient the subject was considered to be a drop-out.

Additional top-up doses up to a maximum total of six were permitted to maintain sedation below a score of five for a procedural length of 24 minutes from the first dose of CNS 7056. Subjects whose MOAA/S score reached five within 24 minutes of the first dose were considered to be failures.

MOAA/S scores of zero were to be avoided in as many subjects as possible.

The minimum time interval between two doses was set at two minutes.

Additional stimuli were randomly simulated at a comparable rate (815/1000 subjects) to those observed in Studies CNS 7056-001 and CNS 7056-002, although no subject had more than four spikes of pain.

The Monte Carlo pharmacodynamic simulations generated 1000 continuous MOAA/S curves for each dosing regimen and these were converted to scores of zero to five and hence to four critical parameters which were either to be minimised (percentage zero scores, drop-outs, failures—i.e. subjects who were "scopable", but whose sedation was not maintained for 24 minutes with a maximum of six top-up doses) or maximised (percentage "scopable" after the loading dose of CNS 7056. The average number of top-ups and, hence, the average total dose of CNS 7056 was also calculated.

Figure 4:
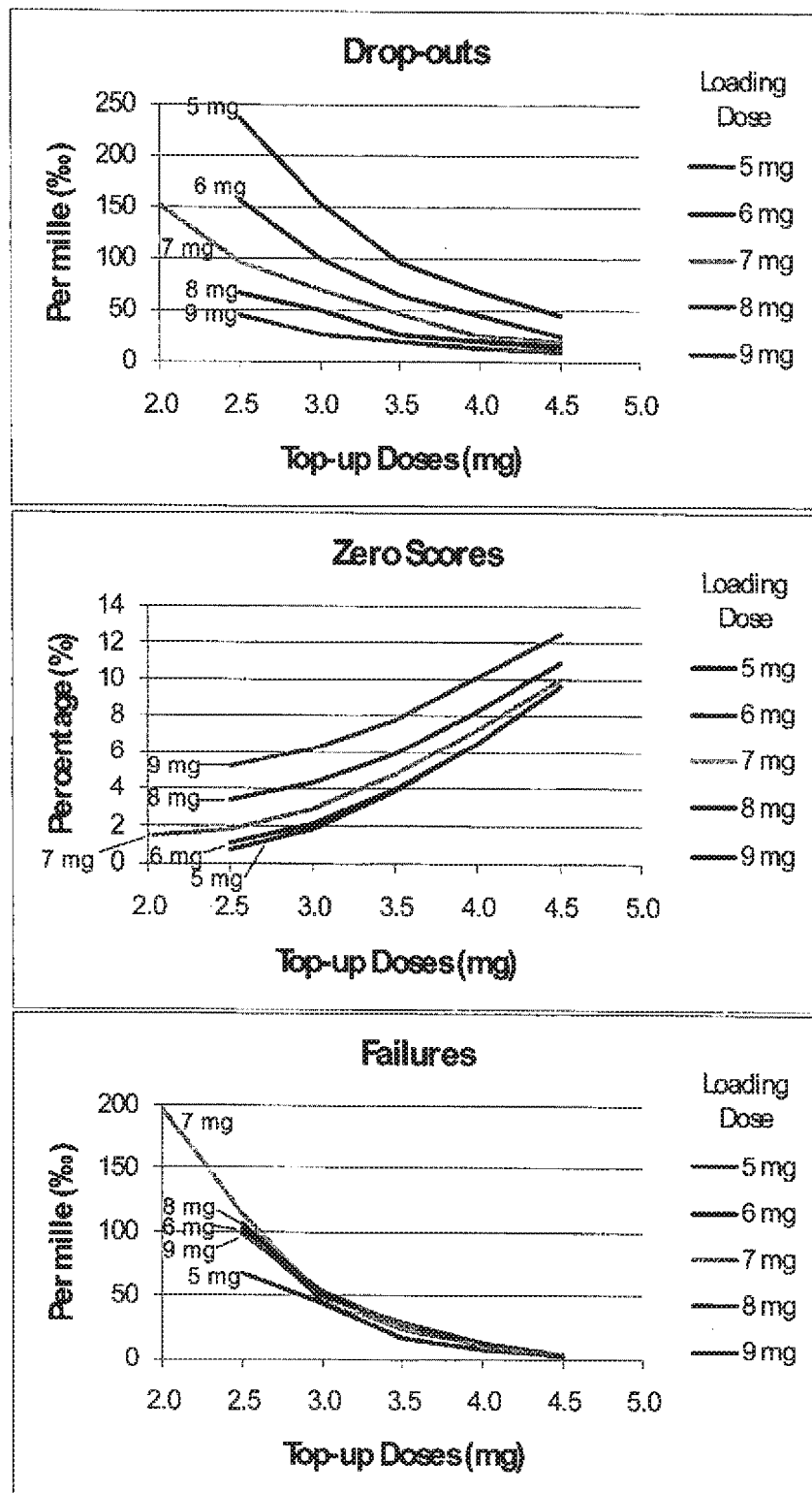

The number of simulated drop-outs depended on both the fixed loading and fixed top-up doses; thus a rate of 5% would be expected after the following dosage regimens: 9/2.5 mg, 8/3 mg, 7/3.5 mg, 6/4 mg and 5/4.5 mg (FIG. 4).

Similarly, 4%-5% zero scores were predicted to be associated with 9/2.5 mg, 8/3 mg and 7/3.5 mg regimens. At the lower 5 and 6 mg loading doses, the zero scores were only governed by the size of the top-ups, 4% following 3.5 mg doses (FIG. 4). The failure rate also depended solely on the size of the top-ups; 5% being predicted to be found by 3 mg doses (FIG. 4). The fraction of simulated subjects whose MOAA/S score was below three after the loading dose of CNS 7056 (i.e. they were considered to have undergone colonoscopy) was 90%, 83%, 72%, 57% and 38% after doses of 9 mg, 8 mg, 7 mg, 6 mg and 5 mg, respectively.

The effect of varying the minimum time intervals between doses of CNS 7056 was studied. Time intervals longer than the standard two minutes would reduce the possibility of failures, patients becoming alert too soon because the maximal permissible number of top-up doses had been taken well before the end of the procedure. For example, the simulations gave a 5% failure-rate on a 6/3 mg dosing regimen with a 2 minute time interval but only 0.2% with 4 minutes (Table 17). However, still longer time intervals increased the failure rate (Table 17). Longer time intervals should also reduce the possibility of over-dosing (and, hence, increased fraction of zero scores) following a "spike" of reduced sedation after an additional stimulus. However, the simulations did not indicate that this was likely and there was no significant reduction in zero scores (Table 17). The danger of a patient becoming fully alert during the procedure would, therefore, probably outweigh the reduction in failure rate. This definition of failure presupposes that the procedure will last for a full 24 minutes; these subjects might not be failures if the colonoscopy were completed earlier or if one additional top-up were employed.

Pharmacodynamic Simulations Based on the CNS 7056-Fentanyl Interaction Analysis

Simulations based on the CNS 7056-fentanyl interaction model gave a similar proportion of drop-outs to the simpler model (e.g. 42‰ versus 44‰ with a 6/4 mg dosing regimen, 50 mcg given four minutes before CNS 7056, Table 18, Table 15), but the number of zero scores was greater (9.95% versus 6.46% with the same regimen). The proportion of "scopable" subjects after the loading dose was slightly higher (604‰ as opposed to 567‰). However, the major difference was in the number of failures, subjects undergoing the procedure but reaching a MOAA/S score of five within 24 minutes of the dose of CNS 7056 despite six top-up doses, (e.g. 86‰ versus 13‰ with a 6/4 mg dosing regimen). All of these differences can be explained by the steeper concentration-response curve of the interaction model (typical Hill coefficients=5.16 and 4.03, Table 19, Table 16).

Figure 5:
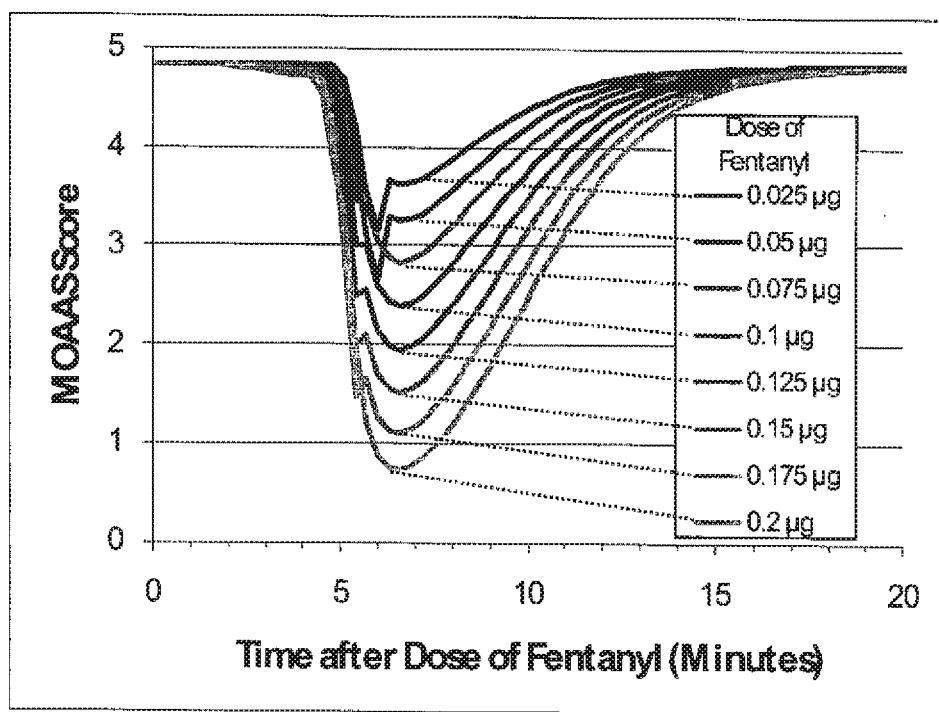
Figure 6:
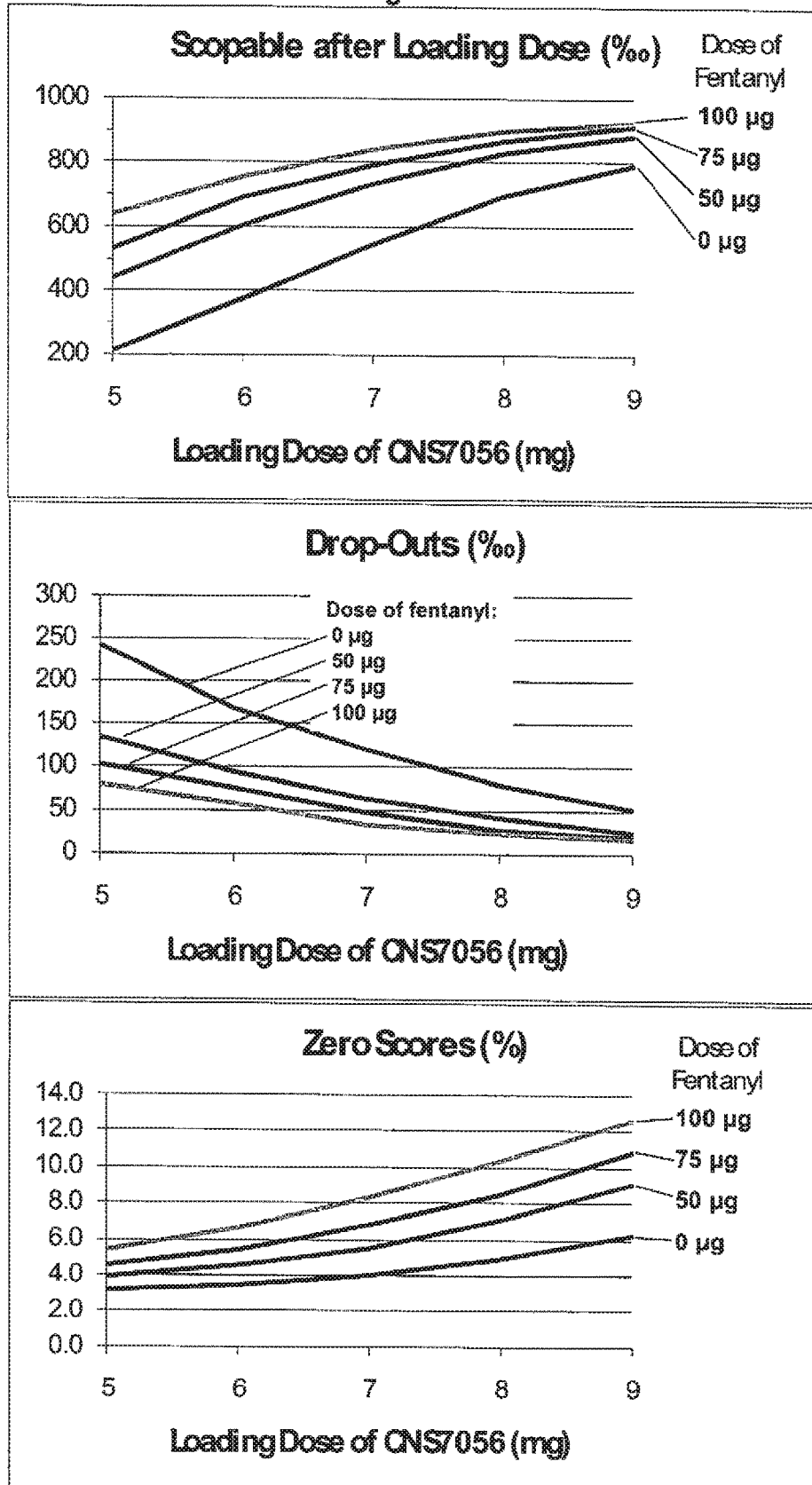

Increasing the doses of fentanyl produced a dose-dependent increase in maximal sedation when combined with a fixed dose of CNS 7056, approximately one MOAA/S unit per 50 mcg of the opioid (FIG. 5). Doubling a 50 mcg dose of fentanyl decreased the drop-out rate by about 40% (e.g. from 9.3% to 5.7% with a 6/3 mg dosing regimen) but increased the number of zero MOAA/S scores by about 40% (FIG. 6, Table 18). The same change in fentanyl dose increased the fraction of subjects "scopable" after the loading dose of CNS 7056 by 5-50% depending on the dose of CNS 7056 (FIG. 6, Table 18), but did not influence the failure rate.

Figure 7:
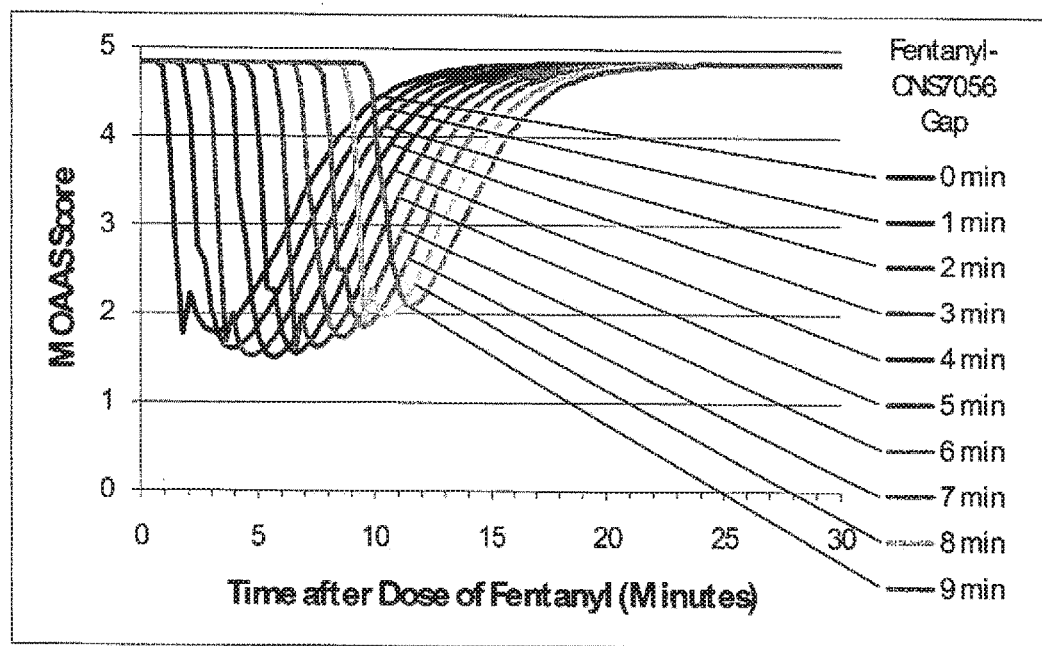

The effect of the CNS 7056-fentanyl interaction was not strongly influenced by the time interval between administration of the two compounds, time intervals of 0-7 minutes giving comparable results in terms of maximal sedation and number of zero scores, drop-outs and failures (FIG. 7, Table 20). Overall, the 8/3 mg dosing regimen would appear to be optimal as the simulations indicate a high proportion of scopable subjects after the loading dose and drop-outs, failures and zero scores all of 5% or less (Table 18, Table 21).

Summary

A data-set consisting of the predominantly arterial CNS 7056 plasma levels from Study CNS 7056-001 has been combined with one made up of the venous concentrations from Study CNS 7056-002 in order that the arterial levels needed for population pharmacodynamic models could be simulated for the latter study.

Physiologically-based pharmacokinetic models with three or four compartments of unknown volume plus pulmonary and arterial compartments, whose volumes were assumed to be proportional to body weight, were fitted to these data.

The modelling indicated that the lung was the primary metabolic organ for CNS 7056 with the liver possibly contributing as little as 10% of the drug's clearance. The pulmonary extraction ratio, and first-pass metabolism, was estimated to be approximately 28%.

Body weight was not a statistically significant predictor of the systemic clearance of CNS 7056 and so dosing in units of mg/kg offers no advantage in terms of consistency of exposure to CNS 7056.

Continuous pharmacodynamic models of MOAA/S scores were fitted to the observed data. The first, simpler model was fitted directly to the raw data and any effects of differences in fentanyl dosing regimens were incorporated into the pharmacodynamic parameters. The second model simulated fentanyl concentrations, using the same historical pharmacokinetic parameters for all subjects, and was able to estimate the pharmacodynamic interaction between CNS 7056 and fentanyl. A 50 mcg dose of fentanyl typically contributed about 5-10% of the sedative effect of a 20 mg total dose of CNS 7056, integrated over the whole procedure. The acute effect was larger, a 50 mcg dose being responsible for an additional maximal fall in MOAA/S score of roughly one unit when combined with CNS 7056.

Both models were refined by the introduction of a "scoping factor", which increased EC50, and described the reduction in sedation resulting from the presence of a colonoscope and a "pain factor", which also increased EC50, and corresponded to sudden "spikes" of increased MOAA/S score.

Despite large improvements in the quality of the models with these modifications, shown by reductions in objective function of several hundred, the observed zero MOAA/S scores were still poorly fitted. This defect was resolved by modifying the zero scores in the data-set to negative values (−1.25 or −1.3). The exact correspondence of the observed and fitted scores was 70% for the final fentanyl-interaction model with 23% of the results differing by one.

The CNS 7056-fentanyl interaction model fitted the observed data significantly better than the simpler model (ΔOFV∼−30). However, its major advantage resulted from its ability to include inter-subject variability in both of the highly variable scoping and concentration-equivalence factors (ΔOFV∼−200).

Monte Carlo simulations of a wide range of dosing regimens suggested that a loading dose of 8 mg of CNS 7056 plus 100 mcg of fentanyl, followed by 3 mg top-up doses at intervals of no less than 2 minutes, would be optimal in terms of minimising drop-outs, MOAA/S scores of zero and failures (subjects whose sedation was not maintained satisfactorily for 24 minutes with 6 top-ups) and maximising the number suitable for insertion of the colonoscope after the loading dose of CNS 7056.

Provided it was not large, the time interval between fentanyl and CNS 7056 dosage made little difference to the simulations, which indicated that the loading dose of CNS 7056 could be given at any time between that of fentanyl and 6-7 minutes later.

Example 2: Phase IIb Study of Remimazolam Vs. Midazolam in Using Combination Fixed Doses Study Design The Phase IIb trial was a double-blind, randomized, parallel group study examining three dose regimens of Remimazolam (CNS 7056) compared with Midazolam in 160 patients undergoing a colonoscopy. The patients received either one of three different initial doses of Remimazolam or Midazolam followed by "top-ups" (i.e. multiple doses) as required to maintain an adequate sedation level to undergo a standard colonoscopy procedure.

The study—conducted in multiple sites in the U.S.—was designed to evaluate the safety of Remimazolam and the success of the sedation, the time to peak sedation as well as the time to full recovery and discharge, in comparison to the gold-standard agent, Midazolam. In addition, based on the results of the successfully concluded Phase Ib and IIa studies, this study was designed to further refine the optimal dose regimen before moving into Phase III.

The following data are based on the ITT (intent to treat) analysis only:

The patients received one of the following doses of Midazolam or Remimazolam:

Midazolam—2.5 mg with 1.0 mg top-ups (40 patients)
Remimazolam—8.0 mg with 3.0 mg top-ups (40 patients)
Remimazolam—7.0 mg with 2.0 mg top-ups (40 patients)
Remimazolam—5.0 mg with 3.0 mg top-ups (40 patients)

The dose of Midazolam was selected as representing the labeled dose. The doses of Remimazolam were selected based on the findings of the three previous clinical trials as predicted by the comprehensive PK/PD analysis (see Example 1).

Results

The success of the procedure was a composite endpoint consisting of sedation sufficient to initiate and complete the procedure, no mechanical or manual ventilation and no rescue sedation. The success rate (ITT) with Midazolam was 75%. The success rate with Remimazolam was 97.5% at the lowest dose regimen, 95% at the middle and 92.5% at the highest dose regimen. A rapid recovery to fully alert (13.3 minutes in the lowest, 11.3 Minutes at the middle and 13.6 Minutes at the highest dose regimen) and short time to discharge (13.5 minutes in the lowest, 14 minutes at the middle and 16.8 minutes at the highest dose regimen) were observed in all Remimazolam treated groups.

The time to fully alert was shorter in the Remimazolam groups when compared to Midazolam. PAION's current interpretation is, that the relatively short wake up times of Midazolam are attributable to the fact that 25% of the midazolam patients did not respond to treatment and therefore received Propofol as a rescue medication quite early which is known as a very short acting compound. Therefore they did not receive "sufficient midazolam" to allow accumulation and resulting in a longer offset times.

This is the first clinical trial with the optimised dose regimen showing clinically relevant improvements of Remimazolam over Midazolam.

Overall, the study showed that it is possible to achieve better results with Remimazolam as compared to the gold standard Midazolam. The safety profile observed in this trial confirmed the good tolerability also shown in all previous studies and as anticipated for a benzodiazepine. There were no unusual findings observed and no patient required manual or mechanical ventilation.

Overall, there was good cardiovascular and respiratory stability with Remimazolam treatment. Compared with the previous Phase Ib study the AESIs (adverse events of special interest) rate was substantially lower due to the revised dosing and study design according to the invention (10 related AESIs in 160 subjects in the Phase IIb study compared to 37 in 45 subjects in the Phase Ib study).

Abbreviations

AUC Area Under the plasma concentration/time Curve
BIS Bispectral Index
Cl Clearance
Clhep Hepatic Clearance
Clpul Pulmonary Clearance
Clsys Systemic Clearance
CRF Case Report Form
ΔOFV Change in Objective Function Value
$EC_{50}$ Concentration leading to half Maximum Pharmacodynamic Effect
$E_{MAX}$ Maximum Pharmacodynamic Effect
$E_{MIN}$ Minimum Pharmacodynamic Effect
ETA (η) NONMEM parameter for inter-individual variability
γ (Gamma) Hill Coefficient—Exponent for Concentrations and $EC_{50}$ in Pharmacodynamic Equation
HPLC High Performance Liquid Chromatography
ICU intensive care unit
IIV Inter-Individual Variability
ke0 Delay Rate Constant between Plasma and the Effect Site
Mm HG Millimeters of Mercury
MOAA/S Modified Observer's Assessment of Alertness and Sedation
MRT Mean Residence Time
OFV Objective Function Value
RSE % Percentage relative standard error
Q (Q2, Q3, Q4) Inter-Tissue Clearance
S.D. Standard Deviation
THETA NONMEM parameter
V1 Central Volume of Distribution
V2 (V3, V4) Peripheral Volume of Distribution
$V_{SS}$ Steady-State Volume of Distribution

LIST OF TABLES

Table 1: Summary of Some Physiologically-Based Population Pharmacokinetic Analyses of CNS 7056 (Studies CNS 7056-001 and CNS 7056-002)
Table 2: Covariate Analysis of Three-Compartment Pharmacokinetic Analysis of CNS 7056 (Run 128S)
Table 3: Comparison of the MOANS Pharmacodynamic Models of Analyses CNS 7056-001, CNS 7056-002 and the Combined Data sets
Table 4: Covariate Analysis of the Effect of Fentanyl on $EC_{50}$ of CNS 7056 in the MOAA/S Pharmacodynamic Analysis.
Table 5: Historical Pharmacokinetic parameters used for Simulations of Fentanyl Plasma Levels.
Table 6: Pharmacodynamic Interactions between Fentanyl and CNS 7056 in the MOANS Analyses (1).
Table 7: Pharmacodynamic Interactions between Fentanyl and CNS 7056 in the MOANS Analyses (2)

Table 8: Effect of the Period of Colonoscopy or Short-lasting Additional Stimuli on $EC_{50}$ of CNS 7056 in the MOAA/S Pharmacodynamic Analysis (1).
Table 9: Effect of the Period of Colonoscopy and Short-lasting Additional Stimuli on $EC_{50}$ of CNS 7056 in the MOAA/S Pharmacodynamic Analysis (2)
Table 10: Pharmacodynamic Interactions between Fentanyl and CNS 7056 in the MOANS Analysis (3)
Table 11: Comparison of CNS 7056-Fentanyl Interaction Pharmacodynamic Analyses in which the Observed MOAA/S "Zero" and "Five" Scores were Modified
Table 12: Comparison of the Three MOAA/S Analyses based on the same Raw Data (Zero Scores changed to −1.30)
Table 13: Comparison of CNS 7056-Fentanyl Interaction MOAA/S Pharmacodynamic Analyses based on Three Pharmacokinetic Models
Table 14: Descriptive Statistics of the Post-Hoc Calculated Parameters of Final Fentanyl-Interaction MOAA/S Pharmacodynamic Analysis for CNS 7056 (CNS 7056 FEN26S)
Table 15: Summary of Monte Carlo Analyses of Various Dosing Regimens of CNS 7056 (Based on Model MOAASALLMIN61S).
Table 16: Summary of Pharmacokinetic and Pharmacodynamic Parameters for CNS 7056 for Monte Carlo Analyses (CNS 7056PBPK128S, MOAASALLMIN61S)
Table 17: Summary of Monte Carlo Analyses of Two Dosing Regimens of CNS 7056 with Varying Minimum time intervals between Top-up Doses (Based on Model MOAASALLMIN61S)
Table 18: Summary of Monte Carlo Analyses of Various Dosing Regimens of CNS 7056 and Fentanyl (Based on Fentanyl-Interaction Model CNS 7056FEN26S)
Table 19: Summary of Pharmacokinetic and Pharmacodynamic Parameters for CNS 7056 for Monte Carlo Analyses (CNS 7056PBPK128S, CNS 7056 FEN26S)
Table 20: Summary of Monte Carlo Analyses of Various CNS 7056-Fentanyl Dosing time intervals (Based on Fentanyl-Interaction Model CNS 7056FEN26S)
Table 21: Summary of Monte Carlo Analyses of Three CNS 7056 Dosing Regimens (Based on Fentanyl-Interaction Model CNS7056FEN26S)
Table 22: Clinical Study (example 2): Superior Response Rate for Remimazolam, (composite primary endpoint: MOAA/S≤4 on 3 consecutive measurements AND completion of colonoscopy procedure AND no requirement for alternative sedative or ventilation)
Table 23: Clinical Study (example 2): Comparison of Success Rates in Colonoscopy (ITT)
Table 24: Clinical study (example 2): Shorter Time to Start of Procedure and low Number of Top-ups
Table 25: Clinical Study (example 2): Short Time to Fully Alert
Table 26: Clinical Study (example 2): Short Time to Ready for Discharge

LIST OF FIGURES

Figure 3:
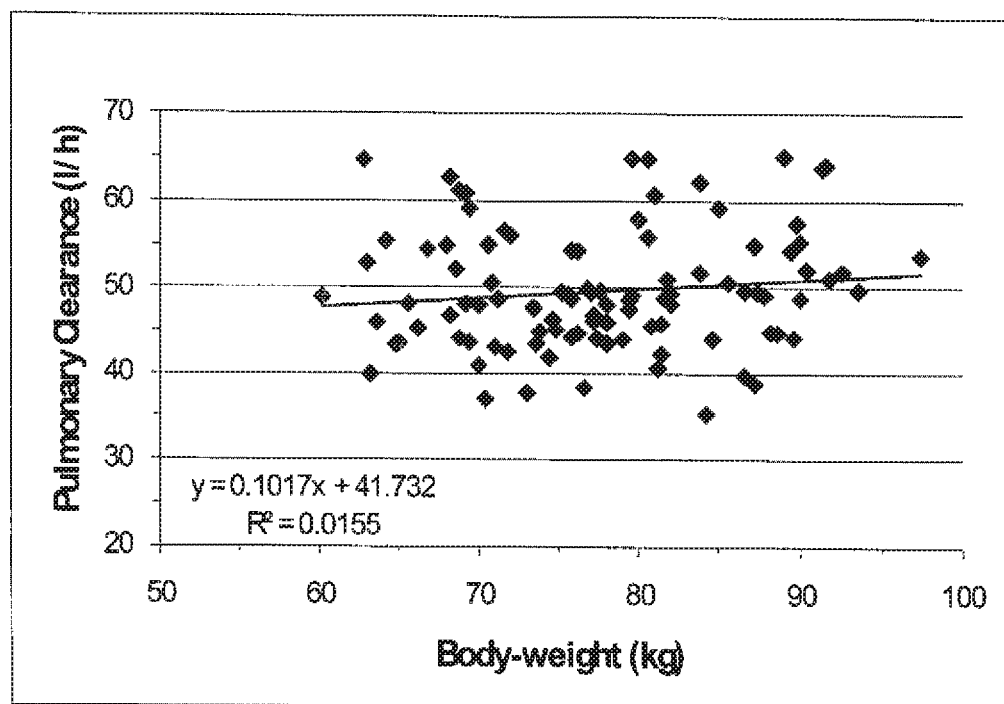

FIG. 1: Doses and success rates in studies CNS 7056-002 and CNS 7056-003. Success was a composite of MOAA/S s 4 on three consecutive measurements and completion of the procedure (including 30 minutes sedation) and no requirement for alternative sedation or ventilation.
FIG. 2: Diagrammatic Representation of Physiologically-based Compartmental Analyses of CNS 7056.
FIG. 3: Plot of Body-weight against Systemic (Pulmonary) Clearance of CNS 7056 after Intravenous Administration at Various Doses (Model CNS 7056PBPK128S.
FIG. 4: Comparison of Monte Carlo Simulated Proportion of Drop-outs, Failures and Zero MOAA/S Scores after Intravenous Administration of CNS 7056 to 1000 Subjects (Based on Model MOAASALLMIN61S).
FIG. 5: Simulated MOAA/S Curves for a Typical Subject after Various Doses of Fentanyl followed, 4 Minutes Later by 7 mg of CNS 7056 (Based on Model MOAASALLFEN26S).
FIG. 6: Comparison of Monte Carlo Simulated Proportions of Drop-outs, Zero MOAA/S Scores and Subjects "Scopable" after Various Dosing Combinations of Fentanyl and CNS 7056 (Top-up Doses kept constant at 3 mg) to 1000 Subjects (Based on Fentanyl-Interaction Analysis CNS 7056 FEN26)
FIG. 7: Simulated MOAA/S Curves for a Typical Subject after a 100 mcg Dose of Fentanyl followed by 8 mg of CNS 7056 after Various Intervals (Based on Model MOAASALLFEN26S)

TABLE 1

| Run Number | 128S | 135S | 142S | 144S |
| --- | --- | --- | --- | --- |
| Number of Individuals/Records | 99/1426 | 99/1426 | 99/1426 | 99/1426 |
| Clearance Organ | Lung | Lung | Lung/Central | Lung/Liver |
| Number of Compartments | 3 | 4 | 3 | 4 |
| Summary of Thetas and RSE %[a] | | | | |
| Blood/Plasma Cardiac Flow (l/h) | 173 (3.37) | 174 (3.59) | 177 (3.54) | 175 (2.68) |
| Pulmonary Clearance (l/h) | 49.1 (2.02) | 48.7 (2.00) | 44.5 (6.11) | 45.0 (4.24) |
| Central Volume (l) | 1.71 (15.2) | 1.24 (19.3) | 1.93 (15.8) | 0.834 (15.8) |
| Inter-Tissue Clearance(4) (l/h) | 74.6 (3.29) | 68.5 (5.45) | 72.4 (3.61) | 46.2 (7.27) |
| Inter-Tissue Clearance(5) (l/h) | 25.7 (6.18) | 42 (5.57) | 25.3 (6.16) | 40 (5.12) |
| Peripheral Volume(4) (l) | 13.5 (9.18) | 8.14 (12.8) | 13.4 (9.32) | 6.47 (13.5) |
| Deep Volume(5) (l) | 23.4 (4.57) | 23.8 (4.78) | 23.1 (4.58) | 22.7 (5.28) |
| Inter-Tissue Clearance(6) (l/h) | | 3.12 (13.2) | | 3.07 (15.1) |
| Deeper Volume(6) (l) | | 12 (20.4) | | 10.9 (16.7) |
| Extra-pulmonary Clearance (l/h) | | | 8.53 (52.4) | 6.15 (49.7) |
| Average Theta RSE % | 6.27 | 9.71 | 12.70 | 13.56 |
| Summary of Etas and RSE %[a] | | | | |
| Pulmonary Clearance (%) | 14.35 (6.07) | 14.42 (6.13) | 17.12 (8.97) | 16.22 (7.32) |
| Central Volume (%) | 146.9 (52.9) | 190.2 (66.8) | 143.6 (52.2) | 368.5 (105.) |
| Peripheral Volume (%) | 50.10 (18.0) | 71.40 (25.4) | 50.48 (18.2) | 90.06 (30.2) |
| Deep Volume (%) | 22.55 (9.94) | 23.44 (10.3) | 22.59 (10.0) | 24.10 (10.9) |
| Average Eta (%) | 58.48 | 74.87 | 58.47 | 124.75 |

TABLE 1-continued

| Run Number | 128S | 135S | 142S | 144S |
|---|---|---|---|---|
| Average Eta RSE % | 21.75 | 27.18 | 22.39 | 38.58 |
| Proportional Error (%) | 21.81 (3.43) | 21.03 (3.24) | 21.74 (3.40) | 20.98 (3.17) |
| Additive Error (±) (µg/ml) | 0.122 (61.8) | 0.111 (60.2) | 0.123 (61.5) | 9.949 (66.5) |
| Objective Function | 8465.96 | 8355.34 | 8463.65 | 8338.55 |
| Objective Function - Baseline | | −110.62 | −2.31 | −127.40 |
| Number of Evaluations (Time Taken) | 451 (0:4:4) | 391 (0:4:13) | 654 (0:5:26) | 869 (0:17:57) |
| Number of Significant Figures | 6.80 | 6.50 | 4.70 | 6.30 |
| Error Messages | None | None | None | None |
| Maximum Eigenvalue ratio | 65.99 | 18.08 | 94.42 | 130514.70 |

[a] Relative standard error (RSE %)

Note:
The compartmental volumes and clearances are numbered as follows: (1) = central, (2) = pulmonary, (3) = arterial, (4) = peripheral, (5) = deep, (6) = deeper, (7) = hepatic.

TABLE 2

| Run | Covariate/Parameter | Factor/Exponent (θ2)[a,b] | Objective Function (OFV) | ΔOFV |
|---|---|---|---|---|
| 128S | | | 8465.96 | — |
| 126S | η/Q | — | 8465.96 | 0.00 |
| 127S | Weight/Q | 0.05 | 8465.92 | −0.04 |
| 130S | Weight/V1 | 2.98 | 8466.48 | 0.53 |
| 137S | Weight/CL | 0.129 | 8464.20 | −1.76 |
| 150S | Sex/V1 | −0.287 | 8483.68 | 17.72 |
| 152S | Weight/V4 | 0.964 | 8462.22 | −3.74 |
| 153S | Weight/V5 | 0.206 | 8465.29 | −0.67 |
| 154S | HR/V1[c] | 2.44 | 8447.20 | −18.76 |
| 155S | HR/Q[c] | −0.424 | 8452.71 | −13.25 |
| 156S | Age/V1 | −0.47 | 8464.43 | −1.53 |
| 157S | HR2/V1[c] | 2.64 | 8451.65 | −14.31 |
| 158S | HR6/V1[c] | 2.53 | 8463.11 | −2.84 |
| 159S | HR/Q, V1[c] | −0.225/2.01 | 8445.74 | −20.22 |

[a] Categorical Covariate – Parameter = θ1 × (1 − Category* θ2) (Category = 1 in males and 0 in females)
[b] Continuous Covariate – Parameter = θ1 × (Covariate Value/Standard)^θ2
(Standard Body-weight = 70 kg, Median age = 37 y, Median Heart-rates = 64, 76, 72 bpm. for pre-dose, 2 minutes and 6 minutes, respectively)
[c] HR, HR2 and HR6 represent heart-rates taken pre-dose and 2 and 6 minutes post-dose, respectively

TABLE 3

| | Summary file | | |
|---|---|---|---|
| | MOAAS001P01S | MOAAS002P01S | MOAASALL01S |
| | Number of Individuals/Records | | |
| | 54/1241 | 45/1523 | 99/2764 |
| Summary of Thetas and (RSE %) | | | |
| EC$_{50}$ (µg/ml) | 0.369 (7.91) | 0.332 (5.18) | 0.349 (4.35) |
| Hill Coefficient (γ) | 3.16 (8.82) | 4.64 (8.81) | 3.92 (6.76) |
| E$_{MIN}$ | 0.0 (—) | 0.0 (—) | 0.0 (—) |
| E$_{MAX}$ | 5.0 (—) | 5.0 (—) | 5.0 (—) |
| ke0 (h$^{-1}$) | 14.3 (6.97) | 15.0 (6.73) | 14.8 (5.08) |
| Average Theta RSE % | 7.91 | 6.91 | 5.399 |
| Summary of Etas and (RSE %) | | | |
| EC$_{50}$ (%) | 49.98 (26.3) | 27.92 (15.3) | 36.02 (15.9) |
| Hill Coefficient (γ) (%) | 44.94 (23.9) | 38.31 (22.3) | 54.49 (23.9) |
| ke0 (%) | 37.41 (22.7) | 34.91 (21.7) | 35.23 (18.3) |
| Average Eta | 44.11 | 33.72 | 41.91 |
| Average Eta RSE % | 24.36 | 19.82 | 19.41 |
| Additive Error (±) | 0.408 (11.8) | 1.140 (15.5) | 0.887 (9.26) |
| Objective Function | −655.81 | 2197.06 | 2641.12 |
| Number of Evaluations (Time Taken) | 216 (0:0:11) | 165 (0:0:15) | 197 (0:0:26) |
| Number of Significant Figures | 4.20 | 5.00 | 4.2 |
| Maximum Eigenvalue ratio | 4.71 | 6.24 | 3.608 |

TABLE 4

| | Summary file | | |
|---|---|---|---|
| | MOAASALL01S | MOAASALL05S | MOAASALL09S |
| | Number of Individuals/Records | | |
| | 99/2764 | 99/2764 | 99/2764 |
| Summary of Thetas and RSE % | | | |
| $EC_{50}$ (μg/ml) | 0.349 (4.35) | 0.364 (5.35) | 0.38 (7.68) |
| Hill Coefficient (γ) | 3.92 (6.76) | 3.9 (7.10) | 3.93 (6.81) |
| $E_{MIN}$ | 0.0 (—) | 0.0 (—) | 0.0 (—) |
| $E_{MAX}$ | 5.0 (—) | 5.0 (—) | 5.0 (—) |
| ke0 ($h^{-1}$) | 14.8 (5.08) | 14.8 (5.10) | 14.9 (5.08) |
| $EC_{50}$ with Fentanyl | | 0.338 (7.36) | |
| Effect of Fentanyl on $EC_{50}$ (θ2) | | | −0.10 (89.4)[a] |
| Average THETA RSE % | 5.399 | 6.232 | 26.741 |
| Summary of Etas and RSE % | | | |
| $EC_{50}$ (%) | 36.02 (15.9) | 35.70 (15.8) | 35.54 (15.7) |
| Hill Coefficient (γ) (%) | 54.49 (23.9) | 54.72 (24.0) | 54.72 (24.0) |
| ke0 (%) | 35.23 (18.3) | 35.07 (18.5) | 35.07 (18.5) |
| Average Eta (%) | 41.91 | 41.84 | 41.78 |
| Average Eta RSE % | 19.41 | 19.47 | 19.44 |
| Additive Error | 0.887 (9.26) | 0.887 (9.30) | 0.887 (9.28) |
| Objective Function | 2641.12 | 2640.27 | 2639.39 |
| Objective Function - Baseline | | −0.85 | −1.73 |
| Number of Evaluations (Time Taken) | 197 (0:0:26) | 238 (0:0:22) | 229 (0:0:23) |
| Number of Significant Figures | 4.2 | 5.6 | 4.9 |
| Maximum Eigenvalue ratio | 3.608 | 4.030 | 7.290 |

[a] $EC_{50} = θ1 × \text{(Scaled Dose)}^{θ2}$, where "scaled dose" = 1 for no fentanyl, 2 for 50 μg and 3 for 75 μg.

TABLE 5

| Parameter | Value |
|---|---|
| Systemic Clearance | 62.4 L/h |
| Inter-Tissue Clearance | 65.4 L/h |
| Central Volume of Distribution | 11.9 L |
| Peripheral Volume of Distribution | 513 L |

TABLE 6

| | Summary file | | | | |
|---|---|---|---|---|---|
| | CNS7056FEN01AS | CNS7056FEN03S | CNS7056FEN04S | CNS7056FEN05S | CNS7056FEN06S |
| | Number of Individuals/Records | | | | |
| | 99/2764 | 99/2764 | 99/2764 | 99/2764 | 99/2764 |
| Summary of THETAs and RSE % | | | | | |
| $EC_{50}$ (μg/ml) | 0.349 (4.38) | 0.348 (—) | 0.342 (4.44) | 0.346 (4.30) | 0.348 (4.39) |
| Hill Coefficient (γ) | 3.9 (6.87) | 3.88 (—) | 4.08 (7.15) | 4.24 (7.52) | 4.4 (5.97) |
| $E_{MIN}$ | 0.0 (—) | 0.0 (—) | 0.0 (—) | 0.0 (—) | 0.0 (—) |
| $E_{MAX}$ | 5.0 (—) | 5.0 (—) | 5.0 (—) | 5.0 (—) | 5.0 (—) |
| ke0 ($h^{-1}$) | 14.8 (5.08) | 15 (—) | 15.1 (4.78) | 14.4 (4.57) | 13.9 (4.70) |
| Conc.-EQ. | | −4.46 (—) | 0.00 (—) | 21.5 (16.6) | 23.7 (30.7) |
| Effect of Scope on $EC_{50}$ | | | 0.116 (5.95) | 0.145 (5.27) | 0.144 (4.92) |
| Average THETA RSE % | 5.45 | — | 5.59 | 7.66 | 10.14 |
| Summary of ETAs and RSE % | | | | | |
| $EC_{50}$ (%) | 36.33 (16.0) | 36.48 (—) | 36.48 (16.0) | 35.54 (15.8) | 35.54 (16.0) |
| Hill Coefficient (γ) (%) | 55.55 (24.3) | 55.43 (—) | 58.80 (25.1) | 60.39 (25.4) | 61.52 (25.5) |
| ke0 (%) | 35.07 (18.2) | 35.07 (—) | 32.36 (16.7) | 31.39 (16.5) | 32.12 (16.8) |
| Conc.-EQ. | | | | | 162.2 (82.6) |
| Average ETA | 42.32 | 42.33 | 42.55 | 42.45 | 72.86 |
| Average ETA RSE % | 19.54 | — | 19.32 | 19.26 | 35.29 |
| Additive Error (±) | 0.886 (9.26) | 0.886 (—) | 0.872 (9.20) | 0.869 (9.30) | 0.854 (9.50) |
| Objective Function | 2637.82 | 2637.10 | 2570.26 | 2554.00 | 2518.82 |
| Objective Function - Baseline | | −0.72 | −67.57 | −83.82 | −119.00 |
| Number of Evaluations (Time Taken) | 189 (0:0:36) | 245 (0:0:51) | 337 (0:1:12) | 350 (0:1:17) | 254 (0:1:11) |
| Number of Significant Figures | 4.50 | 7.60 | 6.50 | 5.30 | 6.00 |
| Error Messages | None | 134 (Rounding Error) | None | None | None |
| Maximum Eigenvalue ratio | 3.59 | 1.00 | 3.62 | 4.47 | 4.67 |

TABLE 7

| | Summary file | | | | | |
|---|---|---|---|---|---|---|
| | CNS7056FEN01AS | CNS7056FEN07S | CNS7056FEN08S | CNS7056FEN09S | CNS7056FEN12S | CNS7056FEN13S |
| | Number of Individuals/Records | | | | | |
| | 99/2764 | 99/2764 | 99/2764 | 99/2764 | 99/2764 | 99/2764 |
| | Length of Stimuli | | | | | |
| | 1 min | ½ min | ½ min | ½ min | ½ min | ½ min |
| Summary of THETAs and RSE % | | | | | | |
| $EC_{50}$ (µg/ml) | 0.349 (4.38) | 0.336 (4.28) | 0.328 (4.48) | 0.331 (4.16) | 0.323 (4.42) | 0.321 (4.33) |
| Hill Coefficient ($\gamma$) | 3.9 (6.87) | 4 (2.6) | 3.96 (6.18) | 4.43 (6.41) | 4.11 (6.54) | 4.18 (7.03) |
| $E_{MIN}$ | 0.0 (—) | 0.0 (—) | 0.0 (—) | 0.0 (—) | 0.0 (—) | 0.0 (—) |
| $E_{MAX}$ | 5.0 (—) | 5.0 (—) | 5.0 (—) | 5.0 (—) | 5.0 (—) | 5.0 (—) |
| ke0 ($h^{-1}$) | 14.8 (5.08) | 14.2 (4.66) | 13.7 (4.30) | 12.8 (4.02) | 14.1 (4.19) | 13.9 (4.51) |
| Effect of Stimulus on $EC_{50}$ | | 1.24 (1.11) | 1.27 (0.85) | 1.23 (0.89) | 1.25 (0.82) | 1.29 (2.43) |
| Conc.-EQ. | | | | 41.3 (7.21) | | |
| Effect of Scope on $EC_{50}$ | | | | 0.155 (4.74) | 0.115 (5.41) | 0.105 (6.2) |
| Average THETA RSE % | 5.45 | 3.17 | 3.96 | 4.58 | 4.28 | 4.90 |
| Summary of ETAs and RSE % | | | | | | |
| $EC_{50}$ (%) | 36.17 (16.0) | 35.86 (15.7) | 35.70 (15.8) | 34.42 (15.9) | 36.17 (16.3) | 35.07 (16.1) |
| Hill Coefficient ($\gamma$) (%) | 55.67 (24.3) | 51.09 (22.1) | 47.95 (20.9) | 52.20 (22.7) | 49.35 (21.9) | 54.25 (23.7) |
| ke0 (%) | 35.07 (18.2) | 32.43 (16.8) | 31.51 (16.1) | 28.25 (15.0) | 29.25 (15.2) | 30.47 (15.9) |
| Effect of Stimulus on $EC_{50}$ | | | | | | 10.70 (8.05) |
| Average ETA | 42.31 | 39.80 | 38.39 | 38.29 | 38.26 | 32.63 |
| Average ETA RSE % | 19.55 | 18.24 | 17.63 | 17.92 | 17.86 | 15.94 |
| Additive Error (±) | 0.886 (9.26) | 0.849 (9.28) | 0.832 (9.38) | 0.814 (9.11) | 0.822 (9.26) | 0.808 (9.14) |
| Objective Function | 2637.23 | 2400.01 | 2285.97 | 2189.77 | 2231.79 | 2200.91 |
| Objective Function - Baseline | | −237.22 | −351.26 | −447.46 | −405.44 | −436.32 |
| Number of Evaluations (Time Taken) | 191 (0:0:38) | 241 (0:1:4) | 214 (0:0:53) | 273 (0:0:58) | 211 (0:0:48) | 263 (0:1:9) |
| Number of Significant Figures | 4.80 | 7.50 | 7.40 | 7.30 | 6.60 | 6.40 |
| Maximum Eigenvalue ratio | 3.58 | 3.64 | 3.76 | 4.68 | 3.71 | 5.52 |

TABLE 8

| | Summary file | | | | | |
|---|---|---|---|---|---|---|
| | MOAASALL01S | MOAASALL18S | MOAASALL21S | MOAASALL22S | MOAASALL23S | MOAASALL33S |
| | Number of Individuals/Records | | | | | |
| | 99/2764 | 99/2764 | 99/2764 | 99/2764 | 99/2764 | 99/2764 |
| | Length of Additional Stimuli | | | | | |
| | 1 min | 1 min | 1 min | 1 min | ½ min | |
| Summary of Thetas and RSE % | | | | | | |
| $EC_{50}$ (µg/ml) | 0.349 (4.35) | 0.342 (4.38) | 0.336 (4.34) | 0.336 (4.31) | 0.329 (4.34) | 0.342 (4.41) |
| Hill Coefficient ($\gamma$) | 3.92 (6.76) | 4.1 (7.04) | 4.02 (6.54) | 3.98 (6.50) | 3.92 (6.09) | 4.21 (7.22) |
| $E_{MIN}$ | 0.0 (—) | 0.0 (—) | 0.0 (—) | 0.0 (—) | 0.0 (—) | 0.0 (—) |
| $E_{MAX}$ | 5.0 (—) | 5.0 (—) | 5.0 (—) | 5.0 (—) | 5.0 (—) | 5.0 (—) |
| ke0 ($h^{-1}$) | 14.8 (5.08) | 15.1 (4.77) | 14.2 (4.65) | 14.4 (4.86) | 14 (4.63) | 15 (4.64) |
| Effect of Scope on $EC_{50}$ | | 0.116 (5.95) | | | | 0.098 (19.8) |
| Effect of Stimulus on $EC_{50}$ | | | 1.25 (1.17) | 0.574 (1.21)[a] | 0.589 (1.03)[a] | |
| Average Theta RSE % | 5.40 | 5.54 | 4.18 | 4.23 | 4.03 | 9.02 |
| Summary of Etas and RSE % | | | | | | |
| $EC_{50}$ (%) | 36.02 (15.9) | 36.17 (15.9) | 35.54 (16.0) | 35.86 (16.2) | 35.86 (16.4) | 36.48 (16.0) |
| Hill Coefficient ($\gamma$) (%) | 54.49 (23.9) | 57.77 (24.8) | 50.35 (22.3) | 51.71 (22.7) | 48.59 (21.4) | 59.37 (25.3) |
| ke0 (%) | 35.23 (18.3) | 32.43 (16.8) | 32.43 (17.0) | 33.27 (16.9) | 31.98 (16.2) | 31.53 (16.4) |
| Effect of Scope on $EC_{50}$ (%) | | | | | | 114.7 (68.5) |
| Average Eta (%) | 41.91 | 42.13 | 39.44 | 40.28 | 38.81 | 60.53 |
| Average Eta RSE % | 19.41 | 19.20 | 18.50 | 18.63 | 18.06 | 31.59 |
| Additive Error (±) | 0.887 (9.26) | 0.874 (9.20) | 0.847 (9.29) | 0.845 (9.31) | 0.830 (9.29) | 0.857 (9.31) |

TABLE 8-continued

| | Summary file | | | | | |
|---|---|---|---|---|---|---|
| | MOAASALL01S | MOAASALL18S | MOAASALL21S | MOAASALL22S | MOAASALL23S | MOAASALL33S |
| | | | Number of Individuals/Records | | | |
| | 99/2764 | 99/2764 | 99/2764 | 99/2764 | 99/2764 | 99/2764 |
| | | | Length of Additional Stimuli | | | |
| | | | 1 min | 1 min | ½ min | |
| Objective Function | 2641.12 | 2573.85 | 2387.30 | 2379.23 | 2269.70 | 2530.09 |
| Objective Function - Baseline | | −67.27 | −253.82 | −261.90 | −371.43 | −111.03 |
| Number of Evaluations (Time Taken) | 197 (0:0:26) | 247 (0:0:29) | 248 (0:0:27) | 259 (0:0:29) | 249 (0:0:29) | 316 (0:0:46) |
| Number of Significant Figures | 4.20 | 4.50 | 4.20 | 5.00 | 4.40 | 4.60 |
| Maximum Eigenvalue ratio | 3.61 | 3.62 | 4.78 | 3.98 | 3.42 | 3.72 |

[a] Size of spike taken into account

TABLE 9

| | Summary file | | | | | |
|---|---|---|---|---|---|---|
| | MOAASALL25S | MOAASALL26S | MOAASALL27S | MOAASALL29S | MOAASALL31S | MOAASALL32S |
| | | | Number of Individuals/Records | | | |
| | 99/2764 | 99/2764 | 99/2764 | 99/2764 | 99/2764 | 99/2764 |
| | | | Length of Additional Stimuli (mins.) | | | |
| | 1 min | ½ min | ½ min | ½ min | ½ min | ½ min |
| Summary of Thetas and RSE % | | | | | | |
| $EC_{50}$ (µg/ml) | 0.332 (4.30) | 0.325 (4.36) | 0.322 (4.28) | 0.323 (4.45) | 0.323 (4.42) | 0.323 (4.48) |
| Hill Coefficient (γ) | 4.12 (6.79) | 4.04 (6.31) | 4.2 (6.88) | 4.05 (6.41) | 4.14 (6.30) | 4.29 (6.57) |
| $E_{MIN}$ | 0.0 (—) | 0.0 (—) | 0.0 (—) | 0.0 (—) | 0.0 (—) | 0.0 (—) |
| $E_{MAX}$ | 5.0 (—) | 5.0 (—) | 5.0 (—) | 5.0 (—) | 5.0 (—) | 5.0 (—) |
| ke0 ($h^{-1}$) | 14.7 (4.54) | 14.2 (4.48) | 13.9 (4.55) | 14.2 (4.59) | 14.1 (4.22) | 14.1 (4.13) |
| Effect of Scope on $EC_{50}$ | 0.103 (6.08) | 0.088 (7.09) | 0.102 (6.38) | 0.098 (6.84) | 0.109 (5.72) | 0.089 (24.5) |
| Effect of Stimulus on $EC_{50}$ | 0.564 (1.08) [d] | 0.58 (0.95) [d] | 1.29 (2.34) | 0.589 (2.34) [d] | 1.25 (0.84) | 1.24 (0.79) |
| Average Theta RSE % | 4.56 | 4.64 | 4.89 | 4.93 | 4.30 | 8.11 |
| Summary of Etas and RSE % | | | | | | |
| $EC_{50}$ | 36.02 (16.1) | 36.02 (16.4) | 34.74 (15.9) | 35.38 (16.4) | 35.86 (16.2) | 36.17 (16.3) |
| Hill Coefficient (γ) | 53.41 (23.6) | 48.34 (22.6) | 52.93 (23.4) | 48.59 (22.0) | 48.34 (21.6) | 51.46 (23.1) |
| ke0 | 30.20 (15.2) | 30.09 (15.5) | 30.58 (15.9) | 30.70 (16.2) | 29.47 (15.2) | 28.76 (14.5) |
| Effect of Stimulus on $EC_{50}$ | | | 10.27 (7.87) | 10.12 (7.54) | | |
| Effect of Scope on $EC_{50}$ | | | | | | 163.3 (100) |
| Average Eta | 39.88 | 38.15 | 32.13 | 31.20 | 37.89 | 69.95 |
| Average Eta RSE % | 18.34 | 18.20 | 15.80 | 15.57 | 17.70 | 38.70 |
| Additive Error (±) | 0.838 (9.34) | 0.825 (9.33) | 0.807 (9.23) | 0.816 (9.36) | 0.821 (9.30) | 0.798 (9.40) |
| Objective Function | 2342.71 | 2244.30 | 2193.54 | 2228.47 | 2221.61 | 2152.84 |
| Objective Function - Baseline | −231.14 [b] | −329.55 [b] | −380.30 [b] | −345.38 [b] | −352.23 [b] | −421.01 [b] |
| Number of Evaluations (Time Taken) | 232 (0:0:26) | 306 (0:0:35) | 344 (0:0:46) | 283 (0:0:38) | 321 (0:0:32) | 489 (0:1:7) |
| Number of Significant Figures | 4.50 | 4.20 | 4.00 | 4.10 | 4.70 | 5.50 |
| Maximum Eigenvalue ratio | 4.59 | 4.08 | 5.62 | 5.10 | 3.76 | 4.13 |

[a] Size of spike taken into account
[b] Relative to MOAASALL18S (Table 8)

TABLE 10

| | Summary file | | | | | |
|---|---|---|---|---|---|---|
| | CNS7056FEN09S | CNS7056FEN10S | CNS7056FEN11S | CNS7056FEN14S | CNS7056FEN18S | CNS7056FEN19S |
| | | | Number of Individuals/Records | | | |
| | 99/2764 | 99/2764 | 99/2764 | 99/2764 | 99/2764 | 99/2764 |
| Summary of THETAs and RSE % | | | | | | |
| $EC_{50}$ (μg/ml) | 0.331 (4.16) | 0.333 (4.50) | 0.328 (4.26) | 0.331 (2.35) | 0.331 (4.44) | 0.333 (4.71) |
| Hill Coefficient (γ) | 4.43 (6.41) | 4.6 (7.32) | 4.41 (7.30) | 4.64 (2.15) | 4.56 (7.12) | 4.69 (6.09) |
| $E_{MIN}$ | 0.0 (—) | 0.0 (—) | 0.0 (—) | 0.0 (—) | 0.0 (—) | 0.0 (—) |
| $E_{MAX}$ | 5.0 (—) | 5.0 (—) | 5.0 (—) | 5.0 (—) | 5.0 (—) | 5.0 (—) |
| ke0 ($h^{-1}$) | 12.8 (4.02) | 12.5 (5.00) | 12.9 (4.20) | 12.4 (1.52) | 12.9 (3.89) | 12.6 (4.36) |
| Effect of Stimulus on $EC_{50}$ | 1.23 (0.89) | 1.22 (0.72) | 1.26 (2.12) | 1.25 (0.88) | 1.22 (0.81) | 1.21 (0.68) |
| Conc.-EQ. | 41.3 (7.21) | 33.1 (29.2) | 33.2 (8.37) | 30.3 (28.8) | 38.3 (7.72) | 28.2 (30.6) |
| Effect of Scope on $EC_{50}$ | 0.155 (4.74) | 0.158 (4.22) | 0.147 (4.97) | 0.143 (4.10) | 0.131 (17.2) | 0.133 (13.9) |
| Average THETA RSE % | 4.58 | 8.50 | 5.21 | 6.64 | 6.88 | 10.09 |
| Summary of ETAs and RSE % | | | | | | |
| $EC_{50}$ (%) | 34.42 (15.9) | 34.74 (16.0) | 33.77 (15.7) | 33.93 (6.97) | 34.91 (15.3) | 35.23 (14.1) |
| Hill Coefficient (γ) (%) | 52.20 (22.7) | 55.20 (24.6) | 54.61 (24.3) | 57.88 (15.0) | 56.49 (23.3) | 59.03 (25.8) |
| ke0 (%) | 28.25 (15.0) | 32.93 (16.2) | 28.95 (15.8) | 32.76 (8.85) | 29.13 (15.0) | 34.09 (15.5) |
| Conc.-EQ. | | 184.1 (91.1) | | 200.0 (78.2) | | 214.1 (113) |
| Effect of Stimulus on $EC_{50}$ | | | 9.277 (7.17) | 8.659 (4.36) | | |
| Effect of Scope on $EC_{50}$ | | | | | 99.28 (60.9) | 90.57 (56.4) |
| Average ETA | 38.29 | 76.77 | 31.65 | 66.66 | 54.96 | 86.61 |
| Average ETA RSE % | 17.92 | 37.04 | 15.78 | 22.71 | 28.69 | 45.05 |
| Additive Error (±) | 0.814 (9.11) | 0.790 (9.44) | 0.803 (9.21) | 0.778 (9.81) | 0.790 (9.51) | 0.767 (9.42) |
| Objective Function | 2189.77 | 2126.25 | 2168.99 | 2102.48 | 2116.61 | 2053.72 |
| Objective Function - Baseline | | −63.52 | −20.79 | −87.29 | −73.17 | −136.05 |
| Number of Evaluations (Time Taken) | 273 (0:0:58) | 432 (0:1:40) | 333 (0:1:12) | 390 (0:1:47) | 298 (0:1:11) | 378 (0:1:40) |
| Number of Significant Figures | 7.30 | 6.10 | 6.20 | 8.20 | 7.50 | 10.10 |
| Maximum Eigenvalue ratio | 4.68 | 5.38 | 7.17 | 13.35 | 5.69 | 6.43 |

TABLE 11

| | Adjusted Score | | Parameters | | Total Scores | | | | | | Predicted/Observed | | | |
|---|---|---|---|---|---|---|---|---|---|---|---|---|---|---|
| Run | "0" | "5" | $E_{MIN}$[e] | $E_{MAX}$[e] | 0 | 1 | 2 | 3 | 4 | 5 | Mean | CV % | Etas | OFV |
| FEN10S | 0.01 | 5.0 | 0 | 5 | 208 | 364 | 291 | 354 | 420 | 1127 | 1.20 | 59.82 | 4[c] | 2126.25 |
| FEN16S | −1.5 | 5.1 | −1.96 | 4.97 | 462 | 187 | 232 | 278 | 437 | 1168 | 1.02 | 16.30 | 4[c] | 3616.30 |
| FEN17S | −1.5 | 5.0 | −1.83 | 4.98 | 468 | 173 | 232 | 270 | 462 | 1159 | 1.01 | 13.30 | 4[c] | 3552.02 |
| FEN19S | 0.01 | 5.0 | 0 | 5 | 230 | 342 | 286 | 347 | 416 | 1143 | 1.18 | 55.16 | 5[cd] | 2053.72 |
| FEN20S | −1.25 | 5.05 | −1.65 | 4.95 | 433 | 211 | 232 | 298 | 447 | 1143 | 1.05 | 21.02 | 4[c] | 3364.80 |
| FEN21S | −1.3 | 5.05 | −1.55 | 4.90 | 452 | 181 | 225 | 291 | 429 | 1186 | 1.02 | 14.52 | 5[cd] | 3293.07 |
| FEN22S | −1.3 | 5.05 | −1.72 | 4.95 | 434 | 211 | 230 | 298 | 446 | 1145 | 1.05 | 21.10 | 4[d] | 3410.00 |
| FEN23S | −1.25 | 5.0 | −1.48 | 4.85 | 450 | 184 | 219 | 295 | 445 | 1171 | 1.02 | 14.82 | 5[cd] | 3216.41 |
| FEN24S | −1.25 | 5.0 | −1.51 | 4.85 | 434 | 202 | 234 | 280 | 454 | 1160 | 1.04 | 19.44 | 4[d] | 3289.08 |
| FEN25S | −1.25 | 5.0 | −1.67 | 4.88 | 436 | 207 | 227 | 301 | 461 | 1132 | 1.05 | 19.77 | 4[c] | 3337.03 |
| FEN26S | −1.3 | 5.0 | −1.54 | 4.84 | 454 | 180 | 219 | 295 | 444 | 1172 | 1.02 | 13.88 | 5[cd] | 3259.55 |
| FEN27S | −1.25 | 5.0 | −1.62 | 4.91 | 430 | 210 | 240 | 305 | 479 | 1100 | 1.06 | 19.85 | 4[b] | 3415.58 |
| FEN28S | −1.25 | 5.0 | −1.45 | 4.87 | 436 | 201 | 236 | 304 | 445 | 1142 | 1.05 | 18.09 | 4[a] | 3408.37 |
| FEN29S | −1.25 | 5.0 | −1.58 | 4.89 | 434 | 211 | 238 | 300 | 457 | 1124 | 1.06 | 20.56 | 3 | 3423.35 |
| FEN30S | 0.01 | 5.0 | −0.105 | 4.94 | 233 | 330 | 297 | 346 | 440 | 1118 | 1.18 | 52.15 | 4[d] | 2109.72 |
| FEN32S | −1.3 | 5.0 | −1.67 | 4.90 | 436 | 204 | 240 | 303 | 478 | 1103 | 1.06 | 18.32 | 4[b] | 3461.03 |
| Observed | — | — | — | — | 435 | 141 | 237 | 330 | 477 | 1144 | — | — | | |

[a]IIV on additional stimulus
[b]IIV on $E_{MIN}$
[c]IIV on equivalence factor
[d]IIV on scoping factor
[e]Integer values of $E_{MAX}$ and $E_{MIN}$ are fixed; all other values are fitted by the model

TABLE 12

| | Summary file | | | | |
|---|---|---|---|---|---|
| | MOAASALLMIN62SC | MOAASALLMIN65SC | CNS7056FEN31S | CNS7056FEN32S | CNS7056FEN26S |
| | Number of Individuals/Records | | | | |
| | 99/2764 | 99/2764 | 99/2764 | 99/2764 | 99/2764 |
| Summary of Thetas and RSE % | | | | | |
| $EC_{50}$ (μg/ml) | 0.367 (5.01) | 0.369 (5.01) | 0.378 (1.51) | 0.375 (1.63) | 0.380 (0.94) |
| Hill coefficient (γ) | 4.20 (7.47) | 4.62 (8.41) | 5.04 (4.12) | 4.30 (2.06) | 5.16 (2.32) |
| $E_{MIN}$ | −1.56 (13.0) | −1.54 (7.20) | −1.57 (2.99) | −1.67 (3.11) | −1.54 (1.75) |
| $E_{MAX}$ | 4.88 (1.20) | 4.85 (0.87) | 4.84 (0.15) | 4.90 (0.31) | 4.84 (0.15) |
| ke0 ($h^{-1}$) | 13.2 (3.83) | 13.2 (4.01) | 12.2 (1.01) | 12.4 (1.38) | 12.1 (0.91) |
| Effect of Additional Stimulus on $EC_{50}$ | 1.28 (1.08) | 1.25 (0.93) | 1.23 (0.54) | 1.26 (0.92) | 1.22 (0.46) |
| Fentanyl concentration-equivalence | | | 40.1 (6.28) | 32.0 (8.87) | 28.0 (24.8) |
| Effect of Scope on $EC_{50}$ | 0.089 (5.75) | 0.058 (35.2) | 0.098 (6.04) | 0.13 (5.34) | 0.101 (4.78) |
| Average Theta RSE % | 5.35 | 8.82 | 2.83 | 2.96 | 4.52 |
| Summary of Etas and RSE % | | | | | |
| $EC_{50}$ | 34.91 (15.8) | 35.23 (14.8) | 32.93 (7.68) | 33.10 (9.51) | 33.43 (6.80) |
| Hill coefficient | 53.17 (23.0) | 69.49 (30.2) | 75.07 (23.0) | 54.25 (11.9) | 77.04 (20.4) |
| $E_{MIN}$ | 29.73 (15.2) | 28.87 (11.7) | 31.91 (8.04) | 29.06 (11.6) | 34.09 (7.12) |
| Effect of Scope on $EC_{50}$ | | 327.1 (186) | 170.1 (58.6) | | 134.2 (45.0) |
| Fentanyl concentration-equivalence | | | | | 192.6 (59.3) |
| $E_{MIN}$ | 94.18 (38.7) | | | 93.78 (38.1) | |
| Average Eta | 53.00 | 115.20 | 77.53 | 52.55 | 94.29 |
| Average Eta RSE % | 23.24 | 60.86 | 24.38 | 17.82 | 27.76 |
| Additive Error (±) | 1.019 (10.3) | 0.993 (10.0) | 0.978 (8.69) | 1.014 (9.35) | 0.952 (9.17) |
| Objective Function | 3480.36 | 3383.98 | 3332.57 | 3461.03 | 3259.55 |
| Objective Function - Baseline | — | — | −51.41 | −19.32 | −73.02 |
| Number of Evaluations (Time Taken) | 277 (0:0:52) | 312 (0:0:56) | 348 (0:2:14) | 439 (0:1:46) | 454 (0:2:12) |
| Number of Significant Figures | 7.50 | 7.20 | 8.20 | 8.40 | 8.40 |
| Maximum Eigenvalue ratio | 10.11 | 9.46 | 91.55 | 90.28 | 18.13 |

TABLE 13

| | Summary file | | |
|---|---|---|---|
| | CNS7056FEN19S[a] | CNS7056FEN135S19[b] | CNS7056FEN159S19[c] |
| | Number of Individuals/Records | | |
| | 99/2764 | 99/2764 | 99/2764 |
| Summary of Thetas and RSE % | | | |
| $EC_{50}$ (μg/ml) | 0.333 (4.71) | 0.339 (1.36) | 0.333 (0.84) |
| Hill coefficient (γ) | 4.69 (6.09) | 4.74 (2.06) | 4.7 (2.34) |
| $E_{MIN}$ | 0.0 (—) | 0.0 (—) | 0.0 (—) |
| $E_{MAX}$ | 5.0 (—) | 5.0 (—) | 5.0 (—) |
| ke0 ($h^{-1}$) | 12.6 (4.36) | 12.8 (1.01) | 12.6 (1.14) |
| Effect of Stimulus on $EC_{50}$ | 1.21 (0.68) | 1.2 (0.40) | 1.21 (0.61) |
| Fentanyl concentration-equivalence | 28.2 (30.6) | 30.9 (20.4) | 28.9 (22.5) |
| Effect of Scope on $EC_{50}$ | 0.133 (13.9) | 0.13 (3.56) | 0.135 (5.21) |
| Average THETA RSE % | 10.09 | 4.81 | 5.45 |
| Summary of Etas and RSE % | | | |
| $EC_{50}$ (%) | 35.23 (14.1) | 35.23 (5.81) | 35.86 (5.67) |
| Hill coefficient (%) | 59.03 (25.8) | 59.49 (13.1) | 59.26 (11.9) |
| $E_{MIN}$ (%) | 34.09 (15.5) | 33.43 (6.71) | 35.70 (7.08) |
| Effect of Scope on $EC_{50}$ (%) | 90.57 (56.4) | 85.42 (27.9) | 84.31 (23.9) |
| Fentanyl concentration-equivalence | 214.1 (113.) | 181.8 (64.9) | 212.8 (78.0) |
| Average ETA | 86.61 | 79.08 | 85.59 |
| Average ETA RSE % | 45.05 | 23.71 | 25.35 |
| Additive Error (±) | 0.767 (9.42) | 0.768 (9.11) | 0.766 (9.53) |
| Objective Function | 2053.72 | 2052.64 | 2048.04 |
| Objective Function - Baseline | — | −1.08 | −5.68 |
| Number of Evaluations (Time Taken) | 378 (0:1:40) | 360 (0:1:52) | 384 (0:1:40) |
| Number of Significant Figures | 10.10 | 8.20 | 8.70 |
| Maximum Eigenvalue ratio | 6.43 | 12.99 | 11.81 |

TABLE 13-continued

| | Summary file | | |
|---|---|---|---|
| | CNS7056FEN26S[a] | CNS7056FEN135S26[b] | CNS7056FEN159S26[c] |
| | Number of Individuals/Records | | |
| | 99/2764 | 99/2764 | 99/2764 |
| Summary of Thetas and RSE % | | | |
| $EC_{50}$ (μg/ml) | 0.380 (0.94) | 0.386 (2.58) | 0.381 (4.17) |
| Hill coefficient (γ) | 5.16 (2.32) | 5.23 (0.54) | 5.19 (0.49) |
| $E_{MIN}$ | −1.54 (1.75) | −1.49 (1.67) | −1.52 (1.76) |
| $E_{MAX}$ | 4.84 (0.15) | 4.84 (0.17) | 4.84 (0.13) |
| ke0 ($h^{-1}$) | 12.1 (0.91) | 12.3 (1.19) | 12.1 (0.69) |
| Effect of Stimulus on $EC_{50}$ | 1.22 (0.46) | 1.21 (0.46) | 1.22 (0.63) |
| Fentanyl concentration-equivalence | 28.0 (24.8) | 30.6 (17.9) | 28.9 (19.9) |
| Effect of Scope on $EC_{50}$ | 0.101 (4.78) | 0.096 (4.23) | 0.104 (19.1) |
| Average THETA RSE % | 4.52 | 3.60 | 5.87 |
| Summary of Etas and RSE % | | | |
| $EC_{50}$ (%) | 33.43 (6.80) | 33.77 (6.08) | 33.77 (5.29) |
| Hill coefficient (%) | 77.04 (20.4) | 77.14 (21.0) | 77.45 (21.0) |
| $E_{MIN}$ (%) | 34.09 (7.12) | 33.10 (6.63) | 36.02 (6.03) |
| Effect of Scope on $EC_{50}$ (%) | 134.2 (45.0) | 117.3 (33.6) | 120.4 (39.7) |
| Fentanyl concentration-equivalence | 192.6 (59.3) | 162.2 (52.3) | 195.1 (62.3) |
| Average ETA | 94.29 | 84.73 | 92.55 |
| Average ETA RSE % | 27.76 | 23.93 | 26.89 |
| Additive Error (±) | 0.952 (9.17) | 0.954 (9.37) | 0.950 (9.38) |
| Objective Function | 3259.55 | 3262.71 | 3255.65 |
| Objective Function - Baseline | — | 3.17 | −3.90 |
| Number of Evaluations (Time Taken) | 454 (0:2:12) | 533 (0:2:50) | 489 (0:2:8) |
| Number of Significant Figures | 8.40 | 8.50 | 8.30 |
| Maximum Eigenvalue ratio | 18.13 | 13.77 | 14.10 |

[a]Three-compartment model,
[b]Four-compartment model,
[c]Three-compartment model with heart-rate predicting cardiac output and central volume

TABLE 14

| | $EC_{50}$ (μg/ml) | Gamma | ke0 ($h^{-1}$) | Concentration-equivalence factor | Scoping Factor |
|---|---|---|---|---|---|
| N | 99 | 99 | 99 | 99 | 36 |
| Mean | 0.385 | 6.435 | 12.35 | 40.78 | 0.178 |
| SD | 0.104 | 3.946 | 3.01 | 45.27 | 0.145 |
| SE | 0.011 | 0.399 | 0.30 | 4.57 | 0.015 |
| Minimum | 0.202 | 1.151 | 5.58 | 5.94 | 0.023 |
| Median | 0.380 | 5.229 | 12.14 | 27.99 | 0.110 |
| Maximum | 0.736 | 21.31 | 23.30 | 330.8 | 0.587 |
| CV % | 27.0 | 61.3 | 24.4 | 111.0 | 81.3 |
| Geometric Mean | 0.372 | 5.480 | 11.98 | 31.65 | 0.129 |
| Mean of the Logs | −0.989 | 1.701 | 2.483 | | |
| SD of the Logs | 0.263 | 0.576 | 0.252 | | |

TABLE 15

| Regimen[a] (mg) | Drop-outs (‰) | Zero MOAA/S Scores (%) | Failures (‰) | Scoped after Loading Dose (‰) | Average Top-ups | Average Total Dose (mg) |
|---|---|---|---|---|---|---|
| 9/4.5[a] | 10 | 12.54 | 2 | 897 | 3.133 | 23.10 |
| 9/4 | 13 | 10.08 | 10 | 897 | 3.344 | 22.38 |
| 9/3.5 | 19 | 7.76 | 27 | 897 | 3.579 | 21.53 |
| 9/3 | 27 | 6.18 | 53 | 897 | 3.869 | 20.61 |
| 9/2.5 | 45 | 6.25 | 99 | 897 | 4.192 | 19.48 |
| 8/4.5 | 15 | 10.87 | 2 | 830 | 3.275 | 22.74 |
| 8/4 | 20 | 8.20 | 13 | 830 | 3.478 | 21.91 |
| 8/3.5 | 26 | 5.89 | 29 | 830 | 3.752 | 21.13 |
| 8/3 | 49 | 4.24 | 50 | 830 | 3.999 | 20.00 |
| 8/2.5 | 67 | 3.30 | 107 | 830 | 4.291 | 18.73 |
| 7/4.5 | 19 | 9.96 | 4 | 719 | 3.428 | 22.43 |
| 7/4 | 25 | 7.20 | 12 | 719 | 3.655 | 21.62 |
| 7/3.5 | 46 | 4.69 | 24 | 719 | 3.876 | 20.57 |
| 7/3 | 69 | 2.91 | 48 | 719 | 4.119 | 19.36 |
| 7/2.5 | 96 | 1.88 | 114 | 719 | 4.400 | 18.00 |
| 7/2 | 151 | 1.42 | 197 | 719 | 4.556 | 16.11 |
| 6/4.5 | 24 | 9.48 | 4 | 566 | 3.591 | 22.16 |
| 6/4 | 45 | 6.54 | 14 | 566 | 3.790 | 21.16 |
| 6/3.5 | 65 | 3.84 | 25 | 566 | 4.000 | 20.00 |
| 6/3 | 97 | 2.07 | 50 | 566 | 4.230 | 18.68 |
| 6/2.5 | 157 | 1.08 | 106 | 566 | 4.377 | 16.94 |
| 5/4.5 | 44 | 9.57 | 3 | 380 | 3.668 | 21.51 |
| 5/4 | 68 | 6.44 | 8 | 380 | 3.859 | 20.44 |
| 5/3.5 | 97 | 3.78 | 17 | 380 | 4.079 | 19.28 |
| 5/3 | 153 | 1.83 | 43 | 380 | 4.218 | 17.65 |
| 5/2.5 | 237 | 0.72 | 68 | 380 | 4.234 | 15.59 |

TABLE 16

| Parameter | Units | Geom. Mean (Typical Value) | Mean of Logs. | S.D. of Logs | Subject 1210 |
|---|---|---|---|---|---|
| Clearance | (l/h) | 49.16 | 3.895 | 0.138 | 43.92 |
| V1 | (l) | 1.770 | 0.571 | 0.979 | 6.107 |
| V2 | (l) | 1.103 | 0.098 | 0.110 | 1.209 |
| V3 | (l) | 0.717 | −0.333 | 0.110 | 0.786 |
| Q4 | (l/h) | 74.56 | | | 74.56 |
| Q5 | (l/h) | 25.74 | | | 25.74 |
| V4 | (l) | 13.68 | 2.616 | 0.420 | 21.59 |
| V5 | (l) | 23.24 | 3.146 | 0.186 | 24.18 |
| Q (Q2, Q3) | (l/h) | 173.4 | | | 173.4 |

TABLE 16-continued

| Parameter | Units | Geom. Mean (Typical Value) | Mean of Logs. | S.D. of Logs | Subject 1210 |
|---|---|---|---|---|---|
| Q1 = (Q − Q4 − Q5) | (l/h) | 73.06 | | | 73.06 |
| $EC_{50}$ | (μg/ml) | 0.363 | −1.023 | 0.274 | 0.180 |
| Hill coefficient | | 4.03 | 1.419 | 0.357 | 6.627 |
| ke0 | ($h^{-1}$) | 13.3 | 2.584 | 0.210 | 12.17 |
| $E_{MIN}$ | | −1.50 a | | | −0.742 |
| $E_{MAX}$ | | 5.0 | | | 5.0 |
| Effect of Pain on $EC_{50}$ | | 1.28 | | | 1.28 |
| Effect of Scope on $EC_{50}$ | | 0.095 | | | 0.095 |
| Weight | (kg) | 77.20 | 4.346 | 0.110 | 84.6 | a: As $E_{MIN}$ was negative, the natural logarithms could not be calculated and its was set to the population mean (−1.50) for all subjects.
The compartmental volumes and clearances are numbered as follows: (1) = central, (2) = pulmonary, (3) = arterial, (4) = peripheral, (5) = deep. V2 (weight/70) and V3 (0.65 × weight/70) are calculated from body-weights.

TABLE 17

| Regimen | Minimum Dosing Gap | Dropouts (‰) | Zero MOAA/S Scores (%) | Failures (‰) | Average Top-ups |
|---|---|---|---|---|---|
| 6/4 | 2 min | 45 | 6.54 | 14 | 3.790 |
| 6/4 | 3 min | 45 | 6.50 | 2 | 3.789 |
| 6/4 | 4 min | 45 | 6.43 | 0 | 3.775 |
| 6/3 | 2 min | 97 | 2.07 | 50 | 4.230 |
| 6/3 | 3 min | 97 | 2.05 | 34 | 4.221 |
| 6/3 | 4 min | 97 | 1.97 | 2 | 4.199 |
| 6/3 | 5 min | 97 | 1.81 | 30 | 3.891 |
| 6/3 | 6 min | 97 | 1.72 | 40 | 3.760 |

TABLE 18

| CNS 7056 Regimen[a] (mg) | Fentanyl Dose (μg) | CNS 7056-Fentanyl Gap (min) | Dropouts (‰) | Zero MOAA/S Scores (%) | Failures (‰) | Scoped after Loading Dose (‰) | Average no. of Top-ups |
|---|---|---|---|---|---|---|---|
| 6/4[a] | 50 | 4 min | 42 | 9.95 | 86 | 604 | 3.955 |
| 6/4 | 75 | 4 min | 28 | 10.6 | 87 | 689 | 3.899 |
| 6/4 | 100 | 4 min | 24 | 11.8 | 83 | 754 | 3.806 |
| 5/3 | 0 | 4 min | 242 | 3.17 | 116 | 211 | 4.205 |
| 5/3 | 50 | 4 min | 133 | 3.88 | 168 | 437 | 4.412 |
| 5/3 | 75 | 4 min | 102 | 4.53 | 175 | 529 | 4.423 |
| 5/3 | 100 | 4 min | 79 | 5.39 | 174 | 637 | 4.394 |
| 6/3 | 0 | 4 min | 168 | 3.42 | 148 | 374 | 4.337 |
| 6/3 | 50 | 4 min | 93 | 4.51 | 197 | 604 | 4.387 |
| 6/3 | 75 | 4 min | 75 | 5.39 | 194 | 689 | 4.335 |
| 6/3 | 100 | 4 min | 57 | 6.60 | 194 | 754 | 4.292 |
| 7/3 | 0 | 4 min | 119 | 4.00 | 161 | 545 | 4.338 |
| 7/3 | 50 | 4 min | 64 | 5.51 | 170 | 735 | 4.31 |
| 7/3 | 75 | 4 min | 47 | 6.83 | 166 | 791 | 4.259 |
| 7/3 | 100 | 4 min | 33 | 8.30 | 166 | 839 | 4.211 |
| 8/3 | 0 | 4 min | 80 | 4.91 | 159 | 694 | 4.295 |
| 8/3 | 50 | 4 min | 42 | 7.08 | 156 | 829 | 4.208 |
| 8/3 | 75 | 4 min | 27 | 8.47 | 162 | 868 | 4.151 |
| 8/3 | 100 | 4 min | 24 | 10.3 | 143 | 897 | 4.072 |
| 9/3 | 0 | 4 min | 52 | 6.20 | 153 | 793 | 4.219 |
| 9/3 | 50 | 4 min | 26 | 9.02 | 147 | 882 | 4.087 |
| 9/3 | 75 | 4 min | 20 | 10.8 | 138 | 913 | 4.017 |
| 9/3 | 100 | 4 min | 18 | 12.6 | 130 | 925 | 3.925 |

[a]Loading dose/Top-up doses

TABLE 19

| Parameter | Units | Geom. Mean (Typical Value) | Mean of Logs. | S.D. of Logs. | Subject 1210 |
|---|---|---|---|---|---|
| Clearance | (l/h) | 49.16 | 3.895 | 0.138 | 43.92 |
| V1 | (l) | 1.770 | 0.571 | 0.979 | 6.107 |
| V2 | (l) | 1.103 | 0.098 | 0.110 | 1.209 |
| V3 | (l) | 0.717 | −0.333 | 0.110 | 0.786 |
| Q4 | (l/h) | 74.56 | | | 74.56 |
| Q5 | (l/h) | 25.74 | | | 25.74 |
| V4 | (l) | 13.68 | 2.616 | 0.420 | 21.59 |
| V5 | (l) | 23.24 | 3.146 | 0.186 | 24.18 |
| Q (Q2, Q3) | (l/h) | 173.4 | | | 173.4 |
| Q1 = (Q − Q4 − Q5) | (l/h) | 73.06 | | | 73.06 |
| $EC_{50}$ | (μg/ml) | 0.380 | −0.989 | 0.263 | 0.269 |
| Hill coefficient | | 5.16 | 1.701 | 0.576 | 6.596 |
| ke0 | ($h^{-1}$) | 12.1 | 2.483 | 0.252 | 6.18 |
| $E_{MIN}$ | | −1.54 | | | −1.54 |
| $E_{MAX}$ | | 4.84 | | | 4.84 |
| Effect of Pain on $EC_{50}$ | | 1.216 | | | 1.216 |
| Effect of Scope on $EC_{50}$ | | 0.129 [a] | −2.05 | 0.837 | 0.230 |
| Fentanyl-equivalence factor | | 28.0 | 3.455 | 0.604 | 126.8 |
| Weight | (kg) | 77.20 | 4.346 | 0.110 | 84.6 |

[a] Geometric mean of the 36 subjects from Study CNS 7056-002 who completed the study.

The compartmental volumes and clearances are numbered as follows: (1) = central, (2) = pulmonary, (3) = arterial, (4) = peripheral, (5) = deep. V2 (weight/70) and V3 (0.65 × weight/70) are calculated from body-weights.

TABLE 20

| CNS 7056 Regimen[a] (mg) | Fentanyl Dose (μg) | CNS 7056-Fentanyl Gap (min) | Dropouts (‰) | Zero MOAA/S Scores (%) | Failures (‰) | Scoped after Loading Dose (‰) | Average no. of Top-ups |
|---|---|---|---|---|---|---|---|
| 6/3[a] | 50 | 0.00 | 89 | 4.75 | 156 | 586 | 4.262 |
| 6/3 | 50 | 1.00 | 86 | 4.79 | 168 | 575 | 4.343 |
| 6/3 | 50 | 1.50 | 88 | 4.98 | 168 | 603 | 4.348 |
| 6/3 | 50 | 2.00 | 89 | 5.04 | 169 | 617 | 4.371 |
| 6/3 | 50 | 2.25 | 86 | 4.79 | 171 | 598 | 4.367 |
| 6/3 | 50 | 2.50 | 91 | 4.69 | 162 | 621 | 4.316 |
| 6/3 | 50 | 3.00 | 95 | 4.68 | 167 | 624 | 4.324 |
| 6/3 | 50 | 3.50 | 91 | 4.70 | 187 | 600 | 4.372 |
| 6/3 | 50 | 4.00 | 93 | 4.51 | 197 | 604 | 4.387 |
| 6/3 | 50 | 4.25 | 98 | 4.54 | 205 | 618 | 4.343 |
| 6/3 | 50 | 4.50 | 96 | 4.71 | 218 | 611 | 4.391 |
| 6/3 | 50 | 5.00 | 99 | 4.66 | 216 | 613 | 4.406 |
| 6/3 | 50 | 6.00 | 106 | 4.33 | 155 | 608 | 4.347 |
| 6/3 | 50 | 9.00 | 116 | 4.02 | 159 | 569 | 4.358 |

[a]Loading dose/Top-up doses

TABLE 21

| CNS 7056 Regimen[a] (mg) | Fentanyl Dose (μg) | CNS 7056-Fentanyl Gap (min)[b] | Dropouts (‰) | Zero MoAA/s Scores (%) | Failures (‰) | Scoped after Loading Dose (‰) | Average no. of Top-ups |
|---|---|---|---|---|---|---|---|
| 8/3[a] | 100 | 0.20 | 24 | 11.275 | 123 | 873 | 3.912 |
| 7/2 | 100 | 0.20 | 76 | 6.2375 | 301 | 800 | 4.649 |
| 5/3 | 100 | 0.20 | 77 | 6.2075 | 158 | 556 | 4.221 |

[a]Loading dose/Top-up doses
[b]CNS 7056 infusion started immediately after fentanyl infusion completed (~12 seconds)

TABLE 22

| | Success rate n/N (%) (ITT) |
|---|---|
| Remimazolam - 8.0/3.0 mg | 37/40 (92.5%), p = 0.066 |
| Remimazolam - 7.0/2.0 mg | 38/40 (95.0%), p = 0.025 |
| Remimazolam - 5.0/3.0 mg | 39/40 (97.5%), p = 0.007 |
| Midazolam - 2.5/1.0 mg | 30/40 (75.0%), p = 0.007 |

Descriptive p values for remimazolam represent pair-wise comparisons between each group and midazolam Descriptive p value for midazolam represents comparison to remimazolam groups combined

TABLE 23

| Drug/dose Clinical Phase tested | Success rate n/N (%) |
|---|---|
| Remimazolam - 8.0/3.0 mg | 37/40 (92.5%) |
| Remimazolam - 7.0/2.0 mg | 38/40 (95.0%) |
| Remimazolam - 5.0/3.0 mg | 39/40 (97.5%) |
| Phase IIb (Study CNS7056-004) | |
| Midazolam 2.5/1.0 mg | 30/40 (75.0%) |
| Phase IIb (Study CNS7056-004) | |
| Remimazolam (combined success rate of 2 highest doses) | 24/29 (82.8%) |
| Phase Ib (Study CNS7056-002) | |
| Fospropofol 6.5 mg/kg (labelled dose)* | Phase II: 18/26 (69.2%) |
| Phase II and Phase III | Phase III: 137/158 (86.7%) |
| Midazolam 0.02 mg/kg* | Phase II: 21/26 (80.8%) |
| Phase II and Phase III | Phase III: 36/52 (69.2%) |

*Success rates taken from fospropofol NDA
Midazolam dose for procedural sedation is 1-2.5 mg initially, with titration doses of 1 mg - equivalent to 0.014-0.036 mg/kg initially, for a 70 kg person

TABLE 24

| | ITT Population | | |
|---|---|---|---|
| Time to | Procedure Start* | Procedure Duration | No. of Top-up |
| All data are means (SD) | (minutes) | (minutes) | Doses |
| Remimazolam - 8.0/3.0 mg | 2.23 (1.44) | 13.80 (6.15) | 1.43 (1.52) |
| Remimazolam - 7.0/2.0 mg | 3.03 (2.17) | 14.33 (5.46) | 2.35 (1.97) |
| Remimazolam - 5.0/3.0 mg | 2.65 (1.42) | 12.90 (4.92) | 1.98 (1.64) |
| Midazolam - 2.5/1.0 mg | 4.80 (3.19) | 13.32 (7.01) | 2.48 (1.77) |

*after initial dose

TABLE 25

| MOAA/S | Time to fully alert (mins)* Mean (SD) ITT population |
|---|---|
| Remimazolam - 8.0/3.0 mg | 13.6 (7.48) |
| Remimazolam - 7.0/2.0 mg | 11.3 (5.69) |
| Remimazolam - 5.0/3.0 mg | 13.3 (7.21) |
| Midazolam - 2.5/1.0 mg | 15.2 (7.43) |

*first of three consecutive MOAA/S scores of 5 after the last injection of study drug

TABLE 26

| | Time to ready for discharge (mins)* Mean (SD) After last injection ITT population |
|---|---|
| Remimazolam - 8.0/3.0 mg | 16.8 (7.54) |
| Remimazolam - 7.0/2.0 mg | 14.0 (6.28) |

TABLE 26-continued

| | Time to ready for discharge (mins)* Mean (SD) After last injection ITT population |
|---|---|
| Remimazolam - 5.0/3.0 mg | 13.5 (4.83) |
| Midazolam - 2.5/1.0 mg | 17.1 (7.33) | first of three consecutive Aldrete scores of ≥9

What is claimed is:

1. A method for inducing general anaesthesia in a subject, comprising administering to the subject:
    (a) 3-[(4S)-8-bromo-1-methyl-6-(2-pyridinyl)-4H-imidazo[1,2-a][1,4]benzodiazepin-4-yl]-propionic acid methyl ester of formula (I)

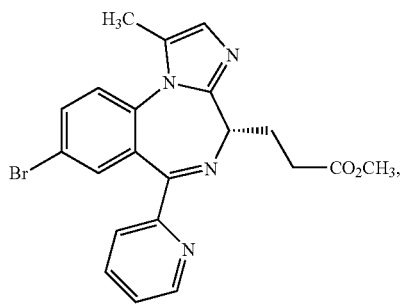

(I)

or a pharmaceutically acceptable salt thereof, in an amount sufficient to induce general anaesthesia in the subject; and
    (b) an analgesic drug; and
    wherein the amount of the compound of formula (I), or a pharmaceutically acceptable salt thereof, administered to the subject does not depend on the body weight of the subject.

2. The method of claim 1, further comprising maintaining general anaesthesia in the subject by administering to the subject a further amount of the compound of formula (I), or a pharmaceutically acceptable salt thereof, and an analgesic drug, wherein the further amount of the compound of formula (I), or a pharmaceutically acceptable salt thereof, administered to the subject does not depend on the body weight of the subject.

3. The method of claim 2, wherein the duration of general anaesthesia in the subject is less than one hour.

4. The method of claim 2, further comprising maintaining a patient airway or positive pressure ventilation in the subject.

5. The method of claim 1, wherein the analgesic drug is an opioid.

6. The method of claim 5, wherein the amount of the opioid administered to the subject does not depend on the body weight of the subject.

7. The method of claim 5, wherein the compound of formula (I), or a pharmaceutically acceptable salt thereof, and the opioid are intravenously administered to the subject.

8. The method of claim 5, wherein the opioid is selected from the group consisting of fentanyl, alfentanil, carfentanil, lofentanil, remifentanil, sufentanil, thiofentanyl, α-methylthiofentanyl, α-methylacetylfentanyl, α-methylfentanyl, ohmefentanyl, β-hydroxy-fentanyl, parafluorfentanyl, and 3-methylfentanyl, or a salt thereof.

9. The method of claim 8, wherein the opioid is remifentanil, or a salt thereof.

10. A method for inducing loss of consciousness in a subject, comprising administering to the subject:
    (a) 3-[(4S)-8-bromo-1-methyl-6-(2-pyridinyl)-4H-imidazo[1,2-a][1,4]benzodiazepin-4-yl]-propionic acid methyl ester of formula (I)

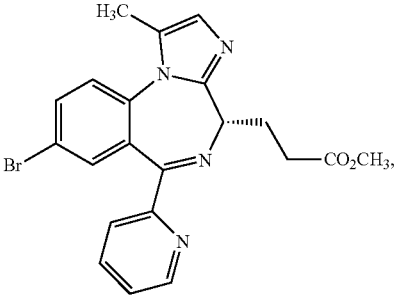

(I)

or a pharmaceutically acceptable salt thereof, in an amount sufficient to induce loss of consciousness in the subject; and
    (b) an analgesic drug; and
    wherein the amount of the compound of formula (I), or a pharmaceutically acceptable salt thereof, administered to the subject does not depend on the body weight of the subject.

11. The method of claim 10, further comprising maintaining loss of consciousness in the subject by administering to the subject a further amount of the compound of formula (I), or a pharmaceutically acceptable salt thereof, and an analgesic drug, wherein the further amount of the compound of formula (I), or a pharmaceutically acceptable salt thereof, administered to the subject does not depend on the body weight of the subject.

12. The method of claim 11, wherein the duration of loss of consciousness in the subject is less than one hour.

13. The method of claim 11, further comprising maintaining a patient airway or positive pressure ventilation in the subject.

14. The method of claim 10, wherein the analgesic drug is an opioid.

15. The method of claim 14, wherein the amount of the opioid administered to the subject does not depend on the body weight of the subject.

16. The method of claim 14, wherein the compound of formula (I), or a pharmaceutically acceptable salt thereof, and the opioid are intravenously administered to the subject.

17. The method of claim 14, wherein the opioid is selected from the group consisting of fentanyl, alfentanil, carfentanil, lofentanil, remifentanil, sufentanil, thiofentanyl, α-methylthiofentanyl, α-methylacetylfentanyl, α-methylfentanyl, ohmefentanyl, β-hydroxy-fentanyl, parafluorfentanyl, and 3-methylfentanyl, or a salt thereof.

18. The method of claim 17, wherein the opioid is remifentanil, or a salt thereof.

19. A method for the induction and maintenance of procedural sedation in a subject, comprising intravenously administering to the subject an initial dose of from about 2 mg to about 10 mg of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, over a one minute time period, wherein the amount of the initial dose does not depend on the body weight of the subject.

20. The method of claim 19, wherein the subject is 18 years or older.

21. The method of claim 19, further comprising administering to the subject one or more supplemental doses of from about 2 mg to about 10 mg of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, over a 15-second time period, wherein the amount of each of the one or more supplemental doses does not depend on the body weight of the subject.

22. The method of claim 21, wherein the one or more supplemental doses of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, is administered to the subject not less than four minutes following administration of the initial dose or a prior supplemental dose.

23. The method of claim 22, wherein the one or more supplemental doses of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, is administered to the subject not less than three minutes following administration of the initial dose or a prior supplemental dose.

24. The method of claim 22, wherein the one or more supplemental doses of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, is administered to the subject not less than two minutes following administration of the initial dose or a prior supplemental dose.

25. The method of claim 19, wherein a dose of an opioid is administered to the subject prior to the initial dose of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof.

26. The method of claim 25, wherein the opioid is fentanyl, or a salt thereof.

27. The method of claim 21, wherein the amount of the one or more supplemental doses of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, administered to the subject is adjusted based on the level of sedation in the subject.

28. The method of claim 27, wherein the amount of the one or more supplemental doses of 3-[(4S)-8-bromo-1-methyl-6-(2-pyridinyl)-4H-imidazo[1,2-a][1,4]benzodiazepin-4-yl]-propionic methyl ester, or a pharmaceutically acceptable salt thereof, administered to the subject is adjusted to induce and maintain the subject in a state of mild to moderate sedation.

* * * * *

UNITED STATES PATENT AND TRADEMARK OFFICE
CERTIFICATE OF CORRECTION

PATENT NO.        : 10,342,800 B2
APPLICATION NO.   : 16/213879
DATED             : July 9, 2019
INVENTOR(S)       : Karin Wilhelm-Ogunbiyi et al.

It is certified that error appears in the above-identified patent and that said Letters Patent is hereby corrected as shown below:

In the Drawings

1. In Fig. 1, Sheet 1 of 7, in Table "B", under "Success rate n/N (%)", Line 3, delete "(64.0)" and insert -- (64.0%) --, therefor.

2. In Fig. 5, Sheet 5 of 7, delete "MOAASScore" and insert -- MOAA/S Score --, therefor.

3. In Fig. 7, Sheet 7 of 7, delete "MOAASScore" and insert -- MOAA/S Score --, therefor.

In the Specification

1. In Column 5, Line 43, delete "(ligand=deltorphine II), the o[sigma]-receptor" and insert -- (ligand=deltorphin II), the σ[sigma]-receptor --, therefor.

2. In Column 14, Line 10, delete "MOAAS/S" and insert -- MOAA/S --, therefor.

3. In Column 14, Line 51, delete "$EC_5$" and insert -- $EC_{50}$ --, therefor.

4. In Column 19, Line 11, delete "lib" and insert -- IIb --, therefor.

5. In Column 20, Line 56, delete "MOANS" and insert -- MOAA/S --, therefor.

6. In Column 20, Line 65, delete "MOANS" and insert -- MOAA/S --, therefor.

7. In Column 20, Line 67, delete "MOANS" and insert -- MOAA/S --, therefor.

8. In Column 21, Line 8, delete "MOANS" and insert -- MOAA/S --, therefor.

9. In Column 22, Line 18, delete "s 4" and insert -- $\leq 4$ --, therefor.

Signed and Sealed this
Twenty-fourth Day of December, 2019

Andrei Iancu
*Director of the United States Patent and Trademark Office*

10. In Columns 31-32, in Table 11, under "Run", Line 4, delete "FEN195" and insert -- FEN19S --, therefor.

11. In Column 35, in Table 15, under "Zero MOAA/S Scores (%)", Line 5, delete "6.25" and insert -- 5.25 --, therefor.

In the Claims

1. In Column 41, Line 66, in Claim 8, delete "parafluorfentanyl," and insert -- parafluorofentanyl, --, therefor.

2. In Column 42, Line 55, in Claim 17, delete "parafluorfentanyl," and insert -- parafluorofentanyl, --, therefor.